(12) United States Patent
Kim et al.

(10) Patent No.: US 7,777,500 B2
(45) Date of Patent: Aug. 17, 2010

(54) METHODS FOR CHARACTERIZING DIELECTRIC PROPERTIES OF PARTS

(75) Inventors: Jaehyun Kim, Fremont, CA (US); Arthur H. Sato, San Jose, CA (US); Keith Comendant, Fremont, CA (US); Qing Liu, Austin, TX (US); Feiyang Wu, San Francisco, CA (US)

(73) Assignee: Lam Research Corporation, Fremont, CA (US)

( * ) Notice: Subject to any disclaimer, the term of this patent is extended or adjusted under 35 U.S.C. 154(b) by 0 days.

(21) Appl. No.: 12/240,414

(22) Filed: Sep. 29, 2008

(65) Prior Publication Data

US 2009/0091335 A1 Apr. 9, 2009

Related U.S. Application Data

(60) Provisional application No. 60/978,082, filed on Oct. 5, 2007, provisional application No. 60/978,085, filed on Oct. 5, 2007, provisional application No. 60/978,087, filed on Oct. 5, 2007, provisional application No. 60/978,089, filed on Oct. 5, 2007.

(51) Int. Cl.
*G01R 27/26* (2006.01)

(52) U.S. Cl. .................. 324/663; 324/639

(58) Field of Classification Search .......... 324/639, 324/663
See application file for complete search history.

(56) References Cited

U.S. PATENT DOCUMENTS

| | | | | |
|---|---|---|---|---|
| 5,065,106 A * | 11/1991 | Hendrick et al. | ........... | 324/663 |
| 6,472,885 B1 * | 10/2002 | Green et al. | ............... | 324/646 |
| 7,205,779 B2 * | 4/2007 | Jennings | ..................... | 324/664 |
| 7,309,982 B2 * | 12/2007 | Navsariwala et al. | ....... | 324/228 |
| 7,479,790 B2 * | 1/2009 | Choi | ......................... | 324/663 |
| 2004/0149699 A1 * | 8/2004 | Hofman et al. | ........ | 219/121.43 |

OTHER PUBLICATIONS

Li et al., Measurement of RF Properties of Glob Top and Under-Encapsulant Materials, Oct. 2001, IEEE, Electrical Performance of Electronic Packaging, pp. 121-124.*

* cited by examiner

*Primary Examiner*—Timothy J Dole
(74) *Attorney, Agent, or Firm*—Martine Penilla & Gencarella, LLP

(57) ABSTRACT

Characterizing dielectric properties of a part includes placing a full-sized part within a dielectric property measurement apparatus. In one embodiment, the full-sized part is a dielectric part of a plasma processing system. The dielectric property measurement apparatus is operated to determine a dielectric constant value of the full-sized part and a loss tangent value of the full-sized part. The determined dielectric constant and loss tangent values are affixed to the full-sized part.

10 Claims, 18 Drawing Sheets

METHODS FOR CHARACTERIZING DIELECTRIC PROPERTIES OF PARTS

CLAIM OF PRIORITY

This application claims priority under 35 U.S.C. 119(e) to each of the following U.S. Provisional Patent Applications: 1) U.S. Provisional Patent Application No. 60/978,082, filed Oct. 5, 2007; 2) U.S. Provisional Patent Application No. 60/978,085, filed Oct. 5, 2007; 3) U.S. Provisional Patent Application No. 60/978,087, filed Oct. 5, 2007; and 4) U.S. Provisional Patent Application No. 60/978,089, filed Oct. 5, 2007. Each of the above-identified provisional patent applications is incorporated herein by reference.

CROSS REFERENCE TO RELATED APPLICATIONS

This application is related to U.S. patent application Ser. No. 12/240,291, filed on even date herewith, entitled "Apparatus for Measuring Dielectric Properties of Parts," and U.S. patent application Ser. No. 12/240,329, filed on even date herewith, entitled "Electrode for Use in Measuring Dielectric Properties of Parts," and U.S. patent application Ser. No. 12/240,375, filed on even date herewith, entitled "Methods for Measuring Dielectric Properties of Parts." The disclosure of each of the above-identified related applications is incorporated herein by reference.

BACKGROUND OF THE INVENTION

Semiconductor wafer ("wafer") fabrication often includes exposing a wafer to a plasma to allow the reactive constituents of the plasma to modify the surface of the wafer. Such plasma processing of a wafer can be performed in a plasma processing system in which a plasma is generated by transmitting radiofrequency (RF) power through a processing gas. The wafer characteristics resulting from the plasma processing operation are dependent on the process conditions, including the plasma conditions. Because the plasma conditions are closely tied to the RF power transmission through the system, it is beneficial to have an accurate knowledge of how the RF power is transmitted through the plasma processing system. Knowledge of how the RF power is transmitted through the plasma processing system is also necessary to match one plasma processing system to another, such that the plasma intensity in each plasma processing system is substantially the same for a given power input. To this end, it is necessary to have an accurate knowledge of the dielectric properties of the plasma processing system parts through which the RF power is transmitted.

Dielectric properties of interest can include the dielectric constant, and loss tangent of a particular part. One conventional technique for measuring dielectric properties of a part includes manufacturing the part with an attached sample coupon that can be removed and subjected to dielectric property measurement. In this conventional technique the sample coupon can be of a small size relative to the actual part. Because the material composition in some parts, e.g., ceramic parts, is subject to spatial variation, there is a potential that the relatively small sample coupon may not provide a true representation of the material composition of the part as a whole. In this situation, the dielectric properties measured for the sample coupon may not be accurate with regard to the actual part as a whole. Also, the dielectric properties of a sample coupon for a given part, as reported by the manufacturer of the given part, may be measured at a frequency that is different than the frequency of the RF power to which the given part will be exposed during use. Because dielectric properties are frequency dependent, the reported dielectric properties of a given part may not be applicable to the frequency of the RF power to which the given part is to be exposed, thereby requiring an extrapolation from the reported dielectric properties of the given part and an assumption of the corresponding extrapolation error.

In view of the foregoing, a solution is needed to enable measurement of the dielectric properties of actual full-sized parts to be used in plasma processing systems, and at the operating frequency of the RF power to which the parts will be exposed during plasma processing operations.

SUMMARY OF THE INVENTION

In one embodiment, a method is disclosed for characterizing dielectric properties of a part. The method includes an operation for placing a full-sized part within a dielectric property measurement apparatus. The method also includes operating the dielectric property measurement apparatus to determine a dielectric constant value of the full-sized part and a loss tangent value of the full-sized part. The method further includes an operation for attaching the determined dielectric constant and loss tangent values to the full-sized part.

In another embodiment, a method is disclosed for characterizing dielectric properties of a dielectric part of a plasma processing system. The method includes an operation for placing a full-sized version of the dielectric part within a dielectric property measurement apparatus. The method also includes operating the dielectric property measurement apparatus to determine a capacitance value of the dielectric part, a resistance value of the dielectric part, a dielectric constant value of the dielectric part, and a loss tangent value of the dielectric part. The method further includes an operation for embossing on the dielectric part each of the dielectric constant and loss tangent values of the dielectric part.

Other aspects and advantages of the invention will become more apparent from the following detailed description, taken in conjunction with the accompanying drawings, illustrating by way of example the present invention.

DETAILED DESCRIPTION

In the following description, numerous specific details are set forth in order to provide a thorough understanding of the present invention. It will be apparent, however, to one skilled in the art that the present invention may be practiced without some or all of these specific details. In other instances, well known process operations have not been described in detail in order not to unnecessarily obscure the present invention.

Figure 1:
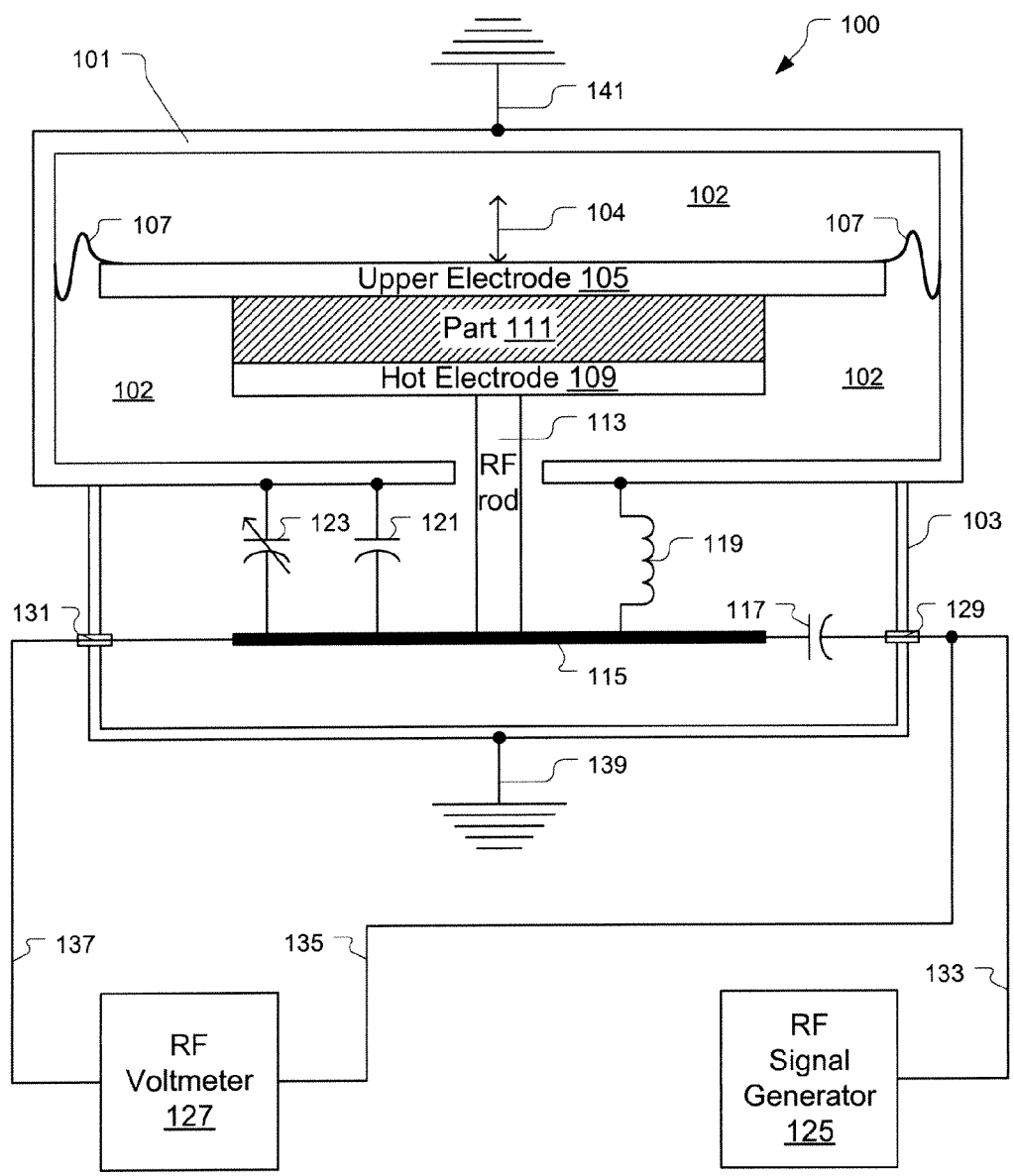
FIG. 1 is an illustration showing an apparatus for measuring dielectric properties of parts, in accordance with one embodiment of the present invention.

FIG. 1 is an illustration showing an apparatus 100 for measuring dielectric properties of parts, in accordance with one embodiment of the present invention. In one embodiment, the parts to have their dielectric properties measured are dielectric components of a plasma processing system. In this embodiment, the parts may correspond to components that will be exposed to RF power during the plasma processing operation, and thereby potentially influence the RF power transmission through the plasma processing system during the plasma processing operation.

The apparatus 100 includes a chamber 101 defined by a conductive material and electrically connected to a ground potential 141. In one embodiment, the chamber 101 is defined by a conductive material of substantially low electrical resistance such as copper. It should be understood, however, that in other embodiments, the chamber 101 can be defined by other low electrical resistance conductive materials, such as aluminum among others. The apparatus 100 also includes an electrical components housing 103 defined by a conductive material and electrically connected to a ground potential 139. In one embodiment, the electrical components housing 103 is positioned below the chamber 101 and is electrically connected to the chamber 101 so as to share a common ground potential with the chamber 101.

The chamber 101 includes an interior cavity 102 defined to house an upper electrode 105 and a hot electrode 109. The upper electrode 105 is disposed in an upper region of the interior cavity 102 over the hot electrode 109. In one embodiment, the upper electrode 105 is defined as a plate of conductive material of low electrical resistance, such as copper. In this embodiment, the upper electrode 105 plate is disposed horizontally in a substantially level orientation within the interior cavity 102. The thickness of the upper electrode 105 can vary so long as a rigidity of the upper electrode 105 is sufficient to maintain a planarity of the upper electrode 105 across the interior cavity 102, and the weight of the upper electrode 105 is not so great as to deform other components that will bear the weight of the upper electrode 105. In the embodiment where the upper electrode 105 is defined as a copper plate, an exemplary upper electrode 105 thickness can vary from about 0.125 inch to about 1 inch. In one particular embodiment, the upper electrode 105 is defined as a copper plate of 0.25 inch thickness.

Also, a size of the upper electrode 105 is defined such that the upper electrode 105 substantially covers a majority of the interior cavity 102 horizontal cross-section area when the upper electrode 105 is positioned in a substantially level orientation within the interior cavity 102. In one embodiment, the upper electrode 105 is sized such that the periphery of the upper electrode 105 extends to within 1 inch to 3 inches of the chamber 101 when the upper electrode is centered within the interior cavity 102 in a substantially horizontal, i.e., level, orientation. Also, in one embodiment, the upper electrode 105 is sized to extend beyond a periphery of a part 111 to be measured by at least twice the vertical thickness of the part 111.

The upper electrode 105 is electrically connected to the chamber 101 by way of peripheral connections 107, thereby placing the upper electrode 105 at the same ground potential as the chamber 101. The peripheral connections 107 are defined to provide a substantially uniform grounding of the upper electrode 105 to the chamber 101 around the periphery of the upper electrode 105. In one embodiment, the peripheral connections 107 are defined by flexible sheets of copper foil. In this embodiment, a solid sheet of flexible copper foil is defined to have a length substantially equivalent to the length of a side of the upper electrode 105. In this embodiment, the flexible copper foil is electrically connected to the upper electrode along the entire length of the edge of the upper electrode 105. Also in this embodiment, the flexible copper foil is electrically connected to the chamber 101 wall proximate to the entire length of the edge of the upper electrode 105. Thus, with an upper electrode 105 defined as a plate having four edges, four flexible copper foil strips are used to respectively connect the four edges of the upper electrode 105 to the chamber 101 wall.

Figure 2A:
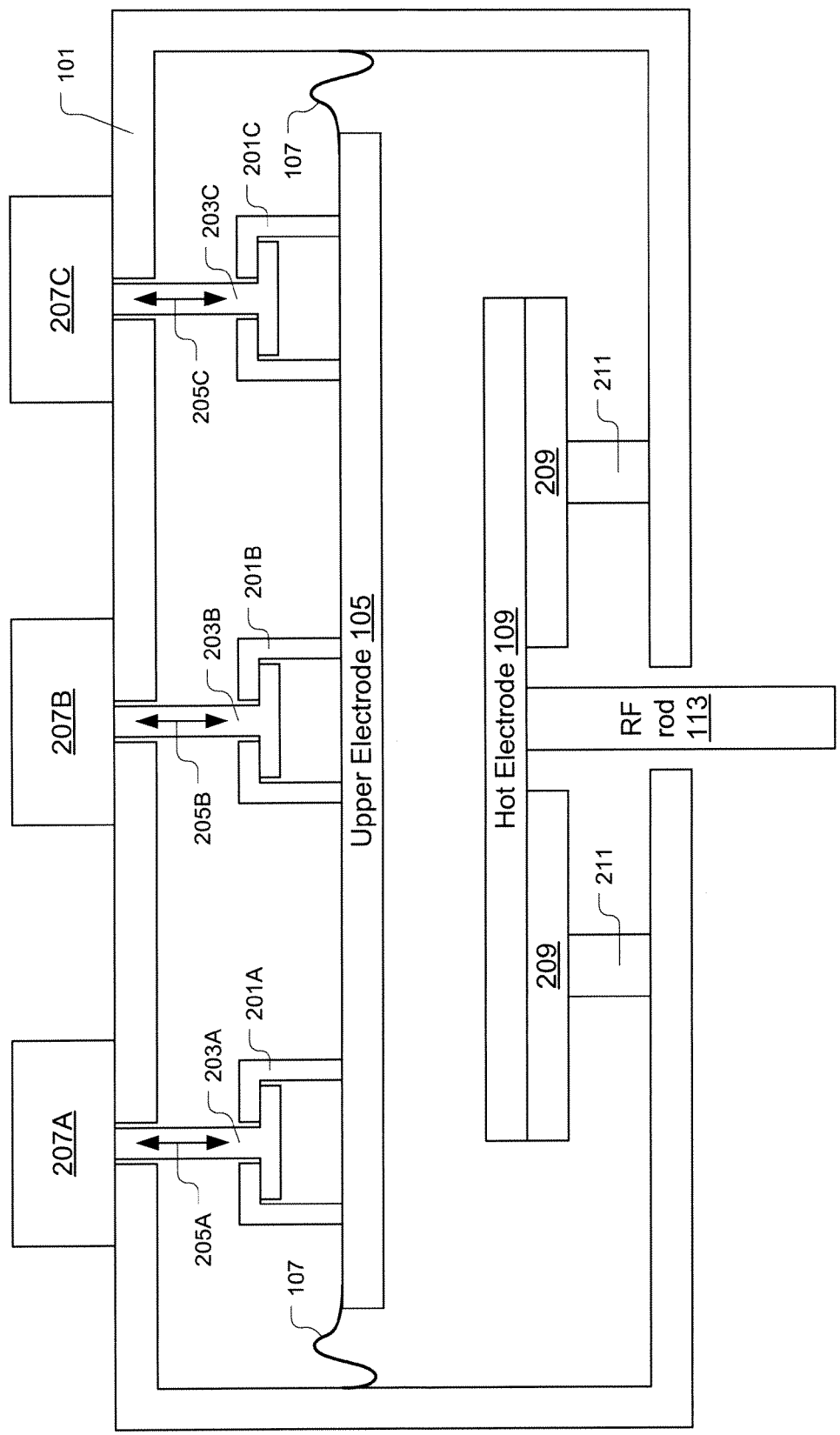
FIG. 2A is an illustration showing the chamber configured to enable vertical movement of the upper electrode, in accordance with one embodiment of the present invention.

The upper electrode 105 is also defined to be moved vertically within the chamber 101, as indicated by arrow 104. FIG. 2A is an illustration showing the chamber 101 configured to enable vertical movement of the upper electrode 105, in accordance with one embodiment of the present invention. In the embodiment of FIG. 2A, three vertical positioning devices 207A-207C are provided at the top of the chamber 101. Each of the vertical position devices 207A-207C is defined to enable vertical position control of a respective lifting member 203A-203C. Each lifting member 203A-203C is defined to have a lifting rod with a disk attached to its lower end. Three guide structures 201A-201C are connected to the top surface of the upper electrode 105. Each guide structure 201A-201C is defined to receive a respective lifting member 203A-203C. More specifically, each guide structure 201A-201C is defined to receive the disk of the lifting member 203A-203C within an internal vertical guide region. Each guide structure 201A-201C is also defined to include a top having an access sized to allow movement of the lifting rod therethrough without allowing movement of the disk of the lifting rod therethrough. Thus, each lifting member 203A-203C is defined to be moved in a vertical direction 205A-205C by its respective vertical positioning device 207A-207C.

The disk portion of each lifting member 203A-203C within each guide structure 201A-201C is defined to engage the underside of the top of the guide structure 201A-201C so as to enable vertical positioning of the upper electrode 105 by way of the lifting members 203A-203C and guide structures 201A-201C. Additionally, in one embodiment, each of the vertical positioning devices 207A-207C includes a vertical position indicator that provides a measure of the vertical position of the lifting member 203A-203C, which in turn provides a measure of the vertical position of the upper electrode 105 in the vicinity of the lifting member 203A-203C. In one embodiment, the vertical position indicators of the vertical positioning devices 207A-207C provide a vertical position measurement to the nearest one-thousandth of an inch.

Figure 2B:
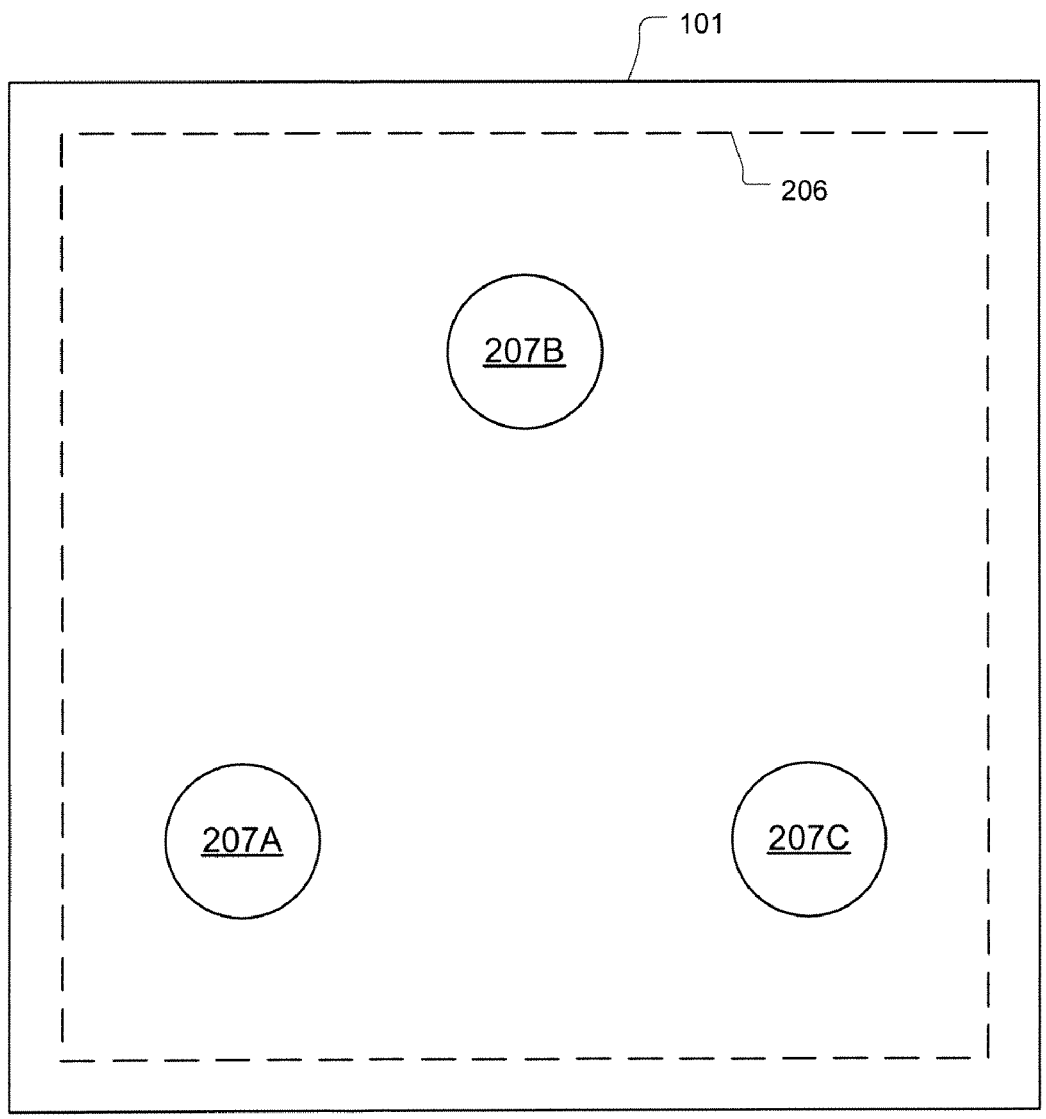
FIG. 2B is an illustration showing a top view of the chamber depicting the relative placement of the three vertical positioning devices, in accordance with one embodiment of the present invention.

In addition to providing vertical elevation control of the upper electrode 105, the three vertical positioning devices 207A-207C are positioned on the top of the chamber 101 to also enable horizontal leveling control of the upper electrode 105 in all directions. FIG. 2B is an illustration showing a top view of the chamber 101 depicting the relative placement of the three vertical positioning devices 207A-207C, in accordance with one embodiment of the present invention. An outline 206 of the periphery of the upper electrode 105 is shown in FIG. 2B. Based on the placement of the three vertical positioning devices 207A-207C, it should be appreciated that through independent control of the vertical positioning devices 207A-207C the horizontal leveling of the upper electrode 105 can be controlled.

Figure 2C:
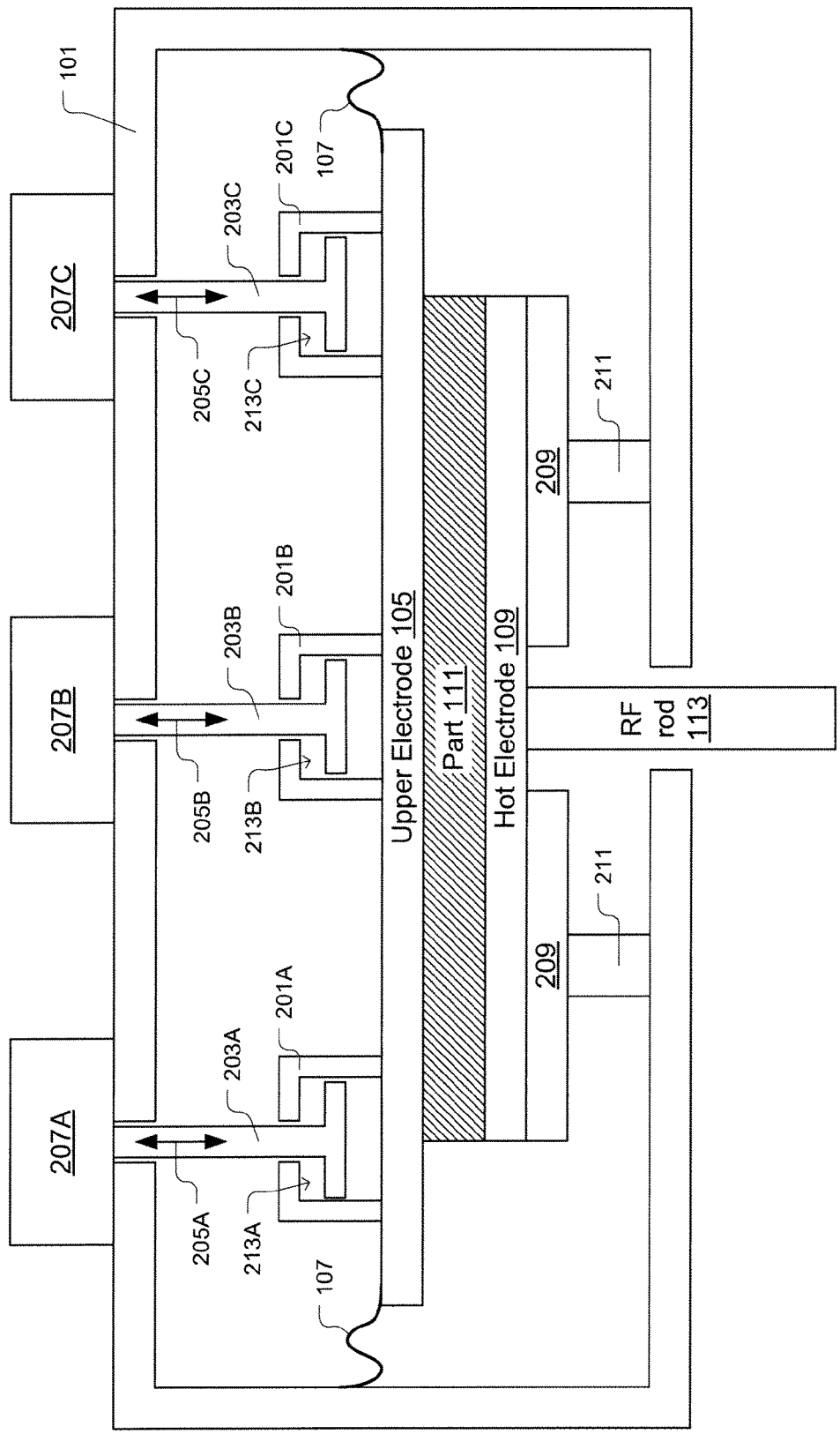
FIG. 2C is an illustration showing the upper electrode lowered so as to rest upon a top surface of a part, in accordance with one embodiment of the present invention.

As discussed in more detail below, during operation of the chamber 101 the upper electrode 105 is lowered so as to rest upon a top surface of a part 111 to be measured. FIG. 2C is an illustration showing the upper electrode 105 lowered so as to rest upon a top surface of a part 111, in accordance with one embodiment of the present invention. To ensure that the upper electrode 105 is allowed to completely rest on top of the part 111, the guide structures 201A-201C are defined to allow the lifting members 203A-203C to be lowered such that their disk members disengage from the top of the guide structures 201A-201C, thereby allowing the upper electrode 105 to rest freely on top of the part 111, as indicated by the gaps 213A-213C between the lifting member 203A-203C disks and the top of the guide structures 201A-201C. It should be appreciated that in this embodiment the contact force between the upper electrode 105 and the part 111 is defined by the weight of the upper electrode 105. Also, it should be understood that the horizontal area size of the grounded upper electrode 105 can remain the same regardless of the size of the part 111 to be measured within the chamber 101.

While the vertical positioning devices 207A-207C and corresponding lifting members 203A-203B and guide structures 201A-201C represent one embodiment for controlling the vertical elevation and horizontal level of the upper electrode 105 within the chamber 101, it should be appreciated that variations of this embodiment can also be used for controlling the vertical elevation and horizontal level of the upper electrode 105. For example, other embodiments can include additional mechanics, such as gears and motors, not explicitly identified herein. Also, other embodiments can include electronic devices, such as motors and sensors, not explicitly identified herein. Also, other embodiments can include data acquisition and control interfaces to enable computer control and monitoring of the various vertical positioning devices 207A-207C, and thereby of the upper electrode 105. Furthermore, it should be appreciated that the peripheral connections 107 are defined to allow the upper electrode 105 to remain electrically connected to the chamber 101 wall as the vertical elevation and horizontal level of the upper electrode 105 is adjusted. In the embodiment where the peripheral connections 107 are defined by sheets of flexible copper foil, the sheets of flexible copper foil are of sufficient size accommodate a full range of vertical movement of the upper electrode 105, within the interior cavity 102 of the chamber 101.

With reference back to FIG. 1, the hot electrode 109 represents a lower electrode within the chamber 101 with respect to the upper electrode 105. The hot electrode 109 is defined to support the part 111 to be measured. The hot electrode 109 is electrically connected to an RF rod 113 through which RF power is conducted to the hot electrode 109 from the RF components within the electrical components housing 103. Both the hot electrode 109 and the RF rod 113 are defined to be electrically isolated from the chamber 101. The hot electrode 109 is positioned within the interior cavity 102 to be far enough away from the grounded chamber 101 walls so as to avoid obscuring a capacitance of the part 111 by the capacitance between the hot electrode 109 and the chamber 101. In one embodiment, the hot electrode 109 is sized as small as possible, but not smaller than the part size 111, so as to minimize the capacitance between the hot electrode 109 and the grounded chamber 101. Both the hot electrode 109 and the RF rod 113 are defined by an electrically conductive material of low electrical resistance, such as copper. The hot electrode 109 is defined to have a vertical thickness sufficient to enable manufacture of the hot electrode 109 without distortion, and to enable support of the combined weight of the part 111 and upper electrode 105 without distortion. In various embodiments, the hot electrode 109 can be defined to have a vertical thickness within a range extending from about 0.125 inch to about 2 inches. In one embodiment, the hot electrode 109 is defined to have a vertical thickness, when disposed within the chamber 101, of about 0.75 inch.

Also, in one embodiment, the hot electrode 109 can be configured to include alignment features to facilitate proper alignment of the part 111 on the hot electrode 109. In one embodiment, proper alignment of the part 111 on the hot electrode 109 is achieved when the part 111 is substantially centered on the top surface of the hot electrode 109. In one embodiment, such as that shown in FIG. 2A, the hot electrode 109 is supported by an electrically insulated support plate 209. In one embodiment, a number of alignment pins are provided in the insulated support plate 209 to enable accurate positioning and alignment of the part 111 on the hot electrode 109. In various embodiments, the support plate 209 can be defined by essentially any type of electrical insulating material. In one embodiment, the support plate 209 is formed from a plastic material. Also, in one embodiment, such as that shown in FIG. 2A, the support plate 209 is further separated from the grounded chamber 101 by a electrically insulated stand 211. In one embodiment the stand 211 is defined by the same material as the support plate 209. In one embodiment, the support plate 209 is defined as a solid plastic disk having an opening in the center through which the RF rod 113 can pass to connect with the hot electrode 109. Also, in this embodiment, the stand 211 is defined as a solid plastic right circular cylinder.

It should be appreciated that the hot electrode 109 is defined to be an interchangeable component of the apparatus 100. Because the sizes of the various parts 111 to be measured will vary, it follows that the size of the hot electrode 109 will also vary. While the size of the hot electrode 109 does not have to exactly match every part 111 to be measured, it is likely that the various parts 111 to be measured will vary sufficiently in size so as to necessitate use of different sized hot electrodes 109. Also, the particular configuration and characteristics of a part 111 to be measured may require use of a hot electrode 109 that is customized in size and shape. For example, if the part 111 includes one or more embedded parts of conductive material, the hot electrode 109 may need to be defined to support the part 111 while also avoiding positioning of the hot electrode 109 beneath the embedded conductive material within the part 111. For instance, if the hot electrode 109 is positioned beneath the embedded conductive material, the embedded conductive material may provide for increased electrical communication between the hot electrode 109 and the upper electrode 105 at the location of the embedded conductive material, which would not be representative of the part 111 as a whole. Because the part 111 to be measured can be of essentially any size and configuration and can include any arrangement of embedded conductive materials, it should be appreciated that the hot electrode 109 can be defined to have essentially any size and configuration as necessary to accommodate the particular characteristics of the part 111 to be measured.

Figure 5A:
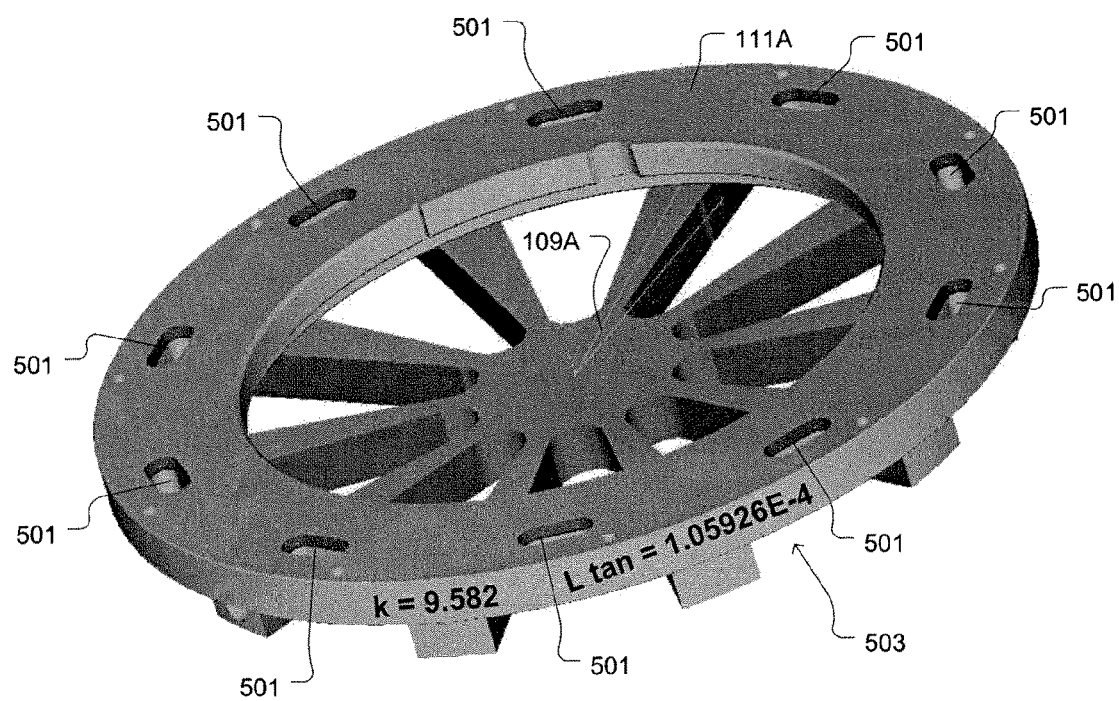
FIG. 5A is an illustration showing an exemplary hot electrode configured to accommodate a ring-shaped part including embedded conductive material, in accordance with one embodiment of the present invention.

FIG. 5A is an illustration showing an exemplary hot electrode 109A configured to accommodate a ring-shaped part 111A including embedded conductive material, in accordance with one embodiment of the present invention. The embedded conductive material is positioned within the ring-shaped part 111A at locations 501. The hot electrode 109A is defined to have a spoked-shape to allow the hot electrode 109A to support the part 111A while simultaneously avoiding placement of the part's embedded conductive material above the hot electrode 109A. Specifically, the hot electrode 109A is defined to be absent at locations 503 below the embedded conductive material locations 501. It should be appreciated that in the same manner that the exemplary hot electrode 109A is specifically configured for the part 111A, other hot electrodes 109 can be specifically configured for other parts 111.

Figure 5B:
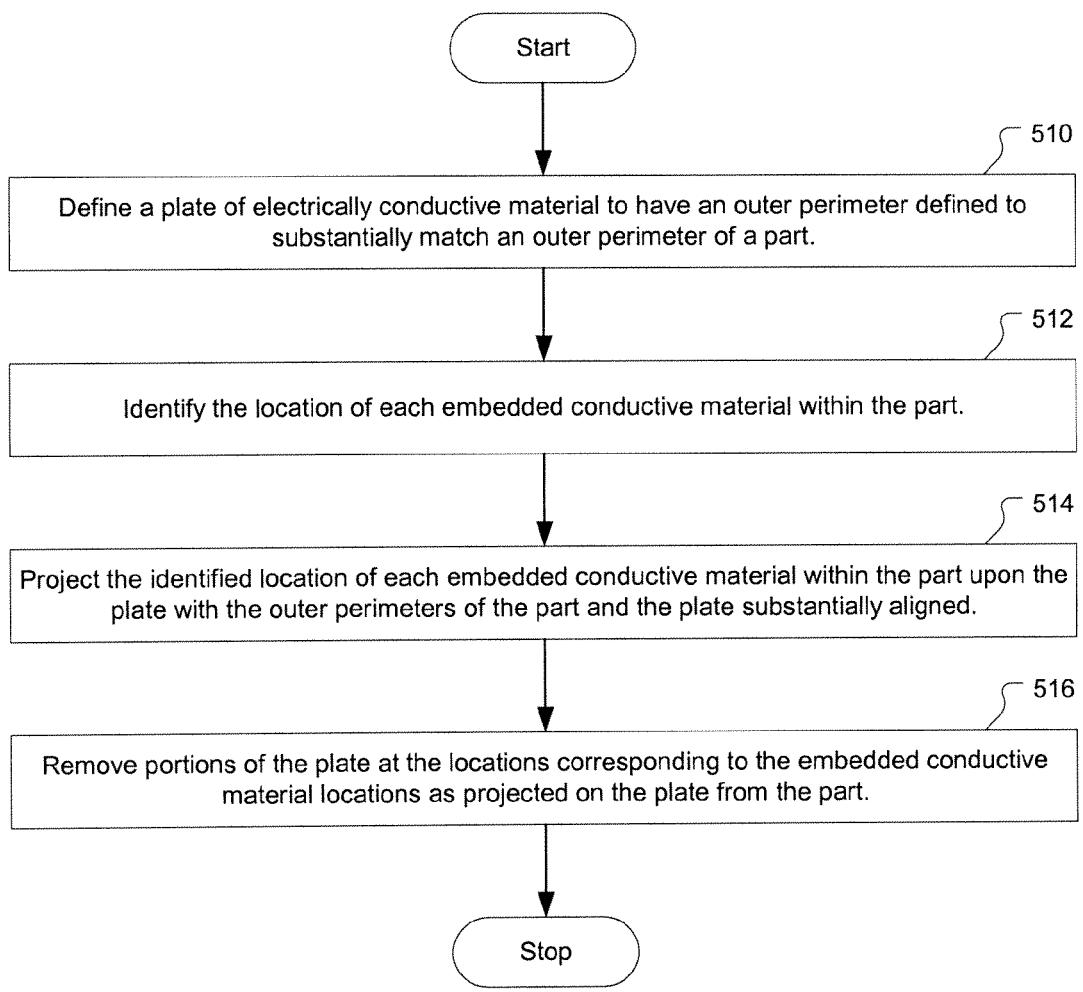
FIG. 5B is a flowchart of a method for configuring the hot electrode for use with a particular part, in accordance with one embodiment of the present invention.

FIG. 5B is a flowchart of a method for configuring the hot electrode 109 for use with a particular part 111, in accordance with one embodiment of the present invention. The method includes an operation 510 for defining a plate of electrically conductive material, such as copper, to have an outer perimeter defined to substantially match an outer perimeter of the part 111. In one embodiment, the part is a dielectric part including a number of embedded conductive materials. The method also includes an operation 512 for identifying the location of each embedded conductive material within the part 111. In an operation 514, the identified location of each embedded conductive material within the part is projected upon the plate with the outer perimeters of the part and the plate substantially aligned. Then, in an operation 516, portions of the plate defining the hot electrode are removed at the locations corresponding to the embedded conductive material locations projected thereon. The size of each removed portion of the hot electrode plate is sufficient to ensure that the hot electrode 109 is not located below the embedded conductive material within the part 111 when the outer perimeters of the part 111 and hot electrode plate 109 are aligned. To the extent possible, operation 516 is performed to ensure that the hot electrode 109 remains a single, contiguous component.

With reference back to FIG. 1, the electrical components housing 103 is defined to house a number of electrical components for conveying the RF power to the RF rod 113 and enabling control of the resonance frequency of the apparatus 100. As a grounded structure, the electrical components housing 103 is also defined to provide RF shielding. The electrical components housing 103 includes a connector 129 to which an RF signal generator 125 is connected via a conductor 133. An RF voltmeter 127 is also connected to the connector 129 via a conductor 135. The electrical components housing 103 also includes a connector 131 to which the RF voltmeter 127 is connected via a conductor 137. In one embodiment, the connectors 129 and 131 are defined as BNC connectors.

The electrical components housing 103 also includes a conductor plate 115 of low electrical resistance material, such as copper, through which the RF power is to be transmitted. The connector 129 is connected through a capacitor 117 to the conductor plate 115 to enable the RF power transmitted from the RF signal generator 125 to be conveyed to the conductor plate 115. The conductor plate 115 is also electrically connected to the connector 131 to enable electrical connection of the RF voltmeter 127 to the conductor plate 115. The electrical components housing 103 further includes an inductor 119, a capacitor 121, and a variable capacitor 123, each of which is electrically connected between the conductor plate 115 and the grounded chamber 101 bottom. In one embodiment, multiple capacitors can be electrically connected between the conductor plate 115 and the grounded chamber 101 bottom to provide an equivalent of the single capacitor 121, as depicted in FIG. 1.

In one embodiment, the capacitor 121 (or its multiple capacitor equivalent) is used to support the conductor plate 115 in a position so as to be electrically separated from the grounded electrical components housing 103, thereby avoiding a short between the conductor plate 115 and the electrical components housing 103. In another embodiment, electrically insulating support brackets can be used to support the conductor plate 115 off of the electrical components housing 103. Additionally, the RF rod 113 is electrically connected to the conductor plate 115 to enable transmission of the RF power from the conductor plate 115 to the hot electrode 109. The variable capacitor 123 can be adjusted to set the resonance frequency of the apparatus 100. For example the variable capacitor 123 can be set so that the resonance frequency of the apparatus 100 is substantially equivalent to the operational frequency of the RF power to be used in the plasma process to which the part 111 is to be exposed.

Figure 3A:
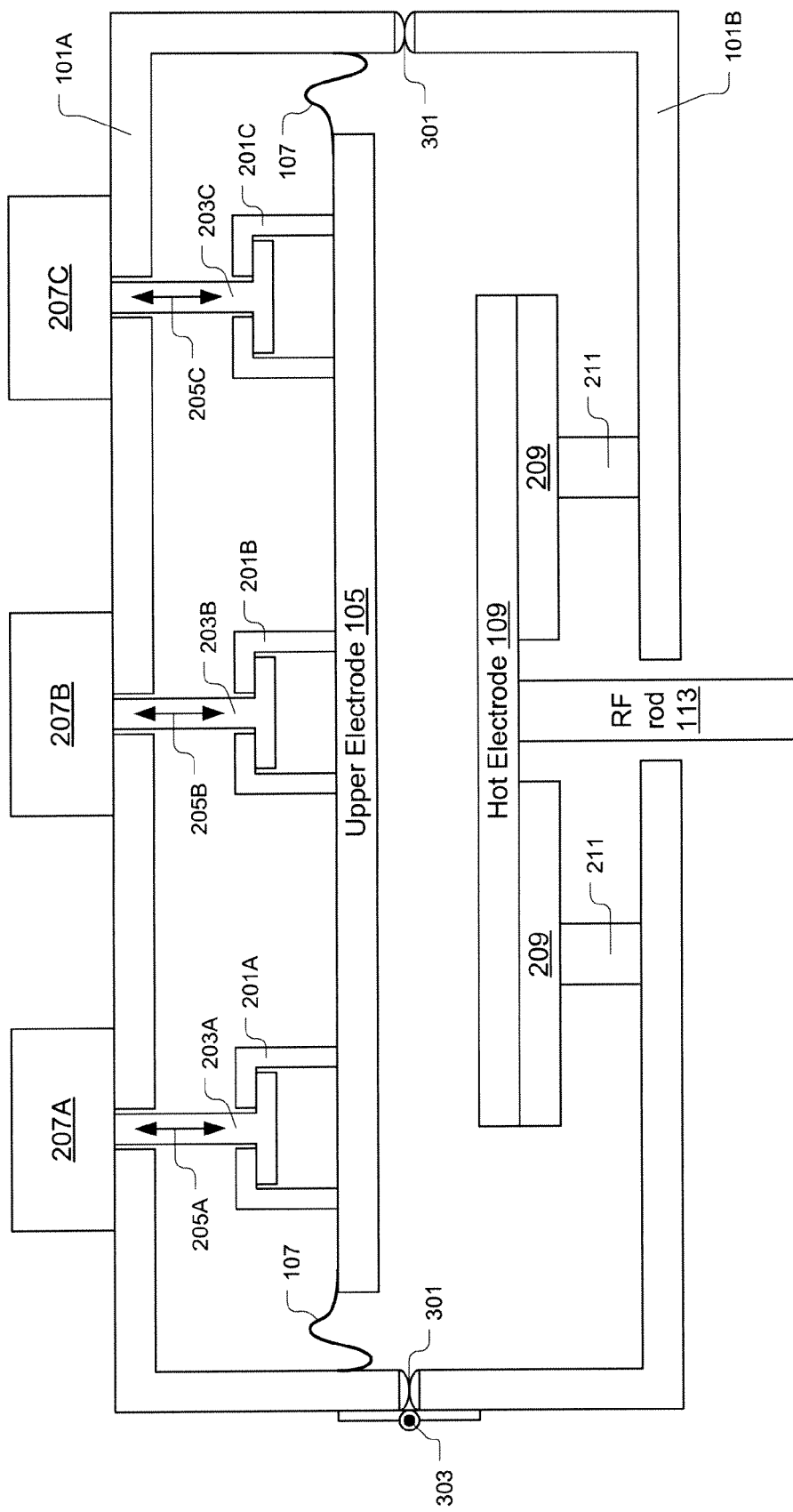
FIG. 3A is an illustration showing a hinged version of the chamber, in accordance with one embodiment of the present invention.
Figure 3B:
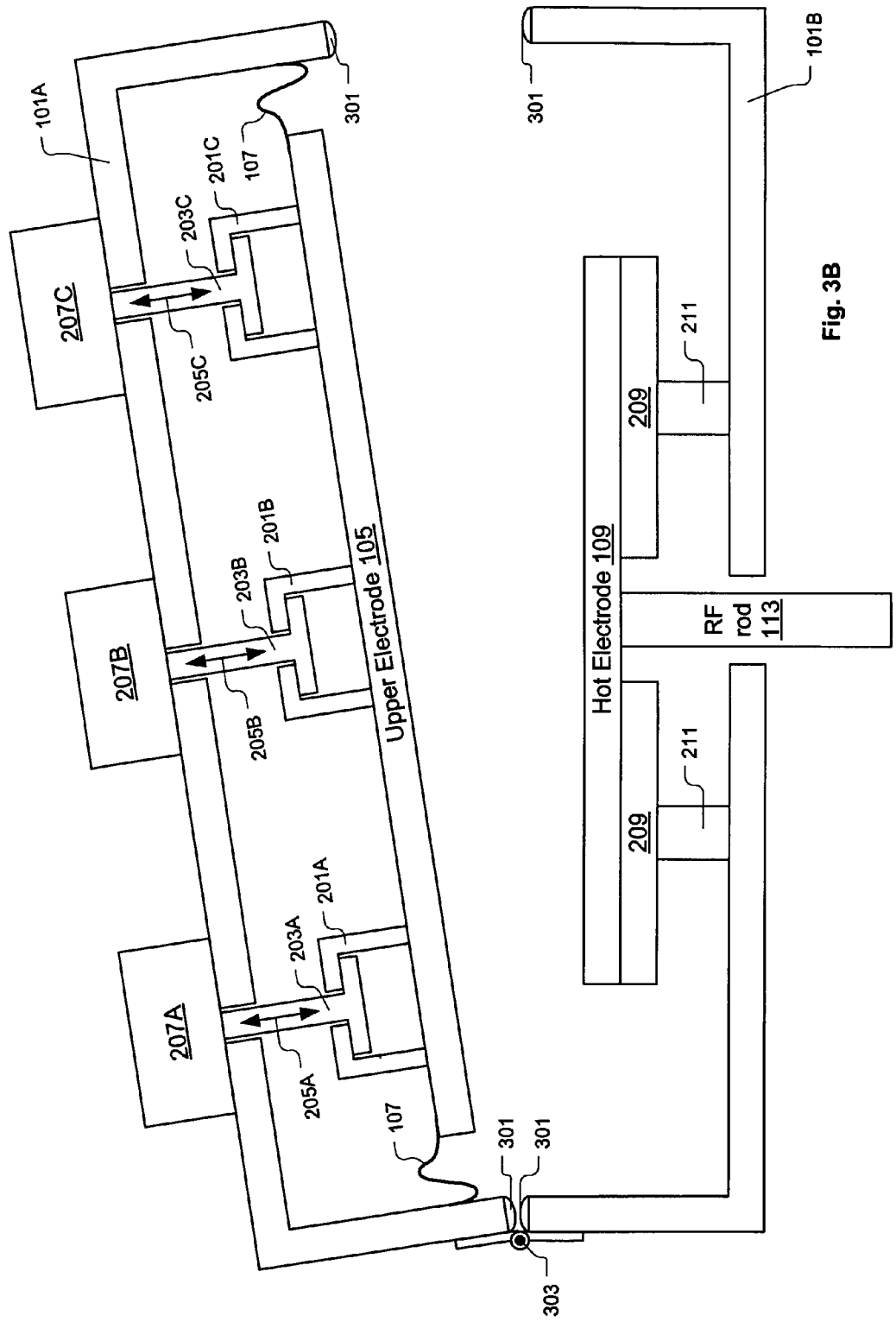
FIG. 3B is an illustration showing the hinged version of the chamber in an open state, in accordance with one embodiment of the present invention.

The chamber 101 can be configured in a number of ways with regard to providing access for placement of the part 111 on the hot electrode 109 and removal of the part 111 from the hot electrode 109. FIG. 3A is an illustration showing a hinged version of the chamber 101, in accordance with one embodiment of the present invention. In the hinged version, the chamber 101 is defined by an upper chamber portion 101A and a lower chamber portion 101B. A hinge 303 is provided to enable opening of the upper chamber portion 101A with respect to the lower chamber portion 101B. FIG. 3B is an illustration showing the hinged version of the chamber in an open state, in accordance with one embodiment of the present invention. In the open state, the part 111 can be easily placed on the hot electrode 109 and retrieved from the hot electrode 109. Also, in the open state, the hot electrode 109 can be accessed for replacement. Also, the hinged version of the chamber utilizes an RF gasket 301 between the upper chamber portion 101A and the lower chamber portion 101B. The RF gasket 301 is defined to provide a uniform electrical connection between the upper chamber portion 101A and the lower chamber portion 101B around the entire periphery of the chamber, so as to ensure that a uniform ground potential exists around the entire periphery of the chamber at the interface between the upper chamber portion 101A and the lower chamber portion 101B. The RF gasket 301 is defined to provide an amount of flexibility to accommodate variations in the interface between the upper and lower chamber portions 101A/101B, thereby ensuring full electrical contact between the upper and lower chamber portions 101A/101B around the periphery of the chamber.

Figure 4A:
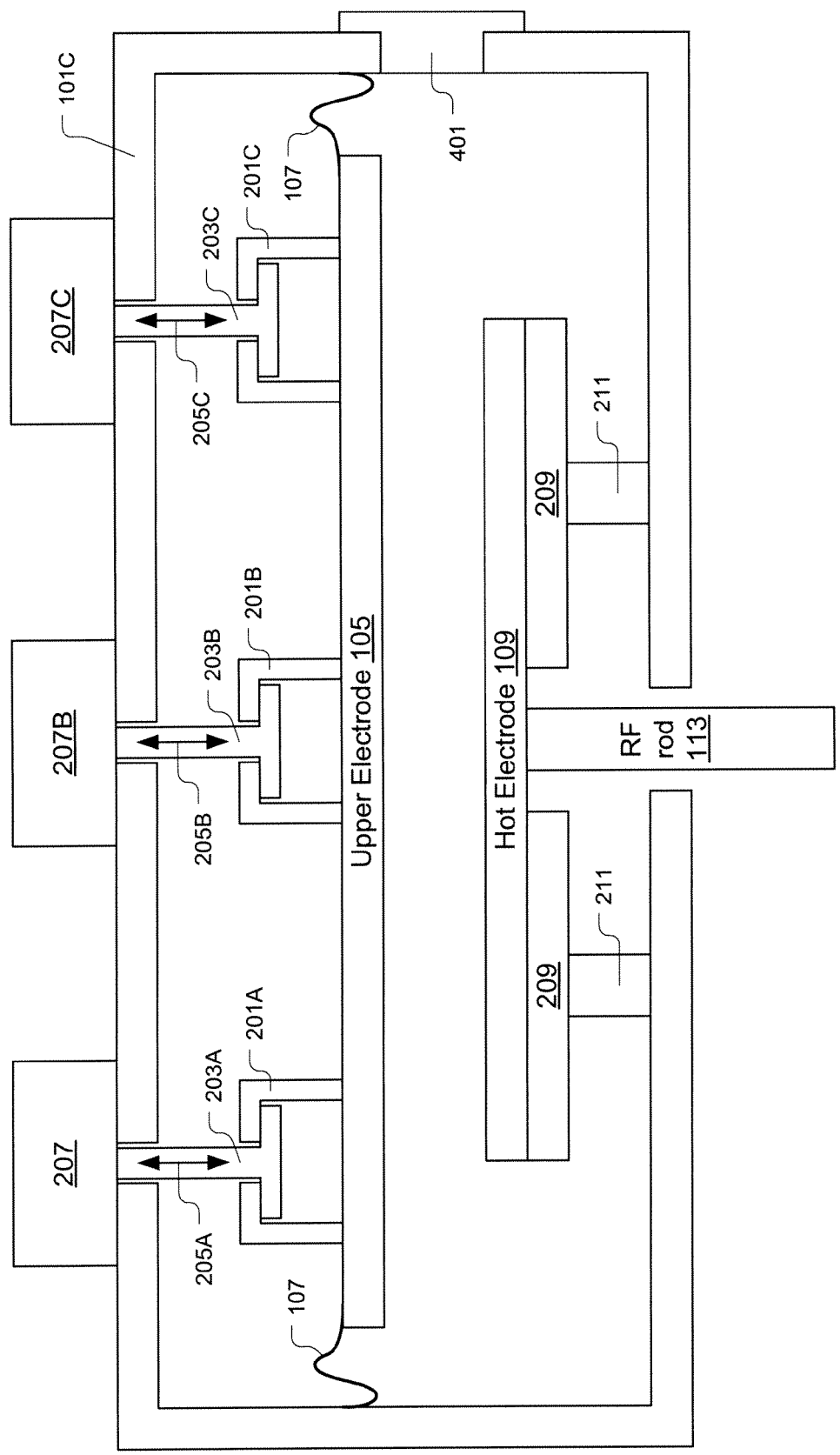
FIG. 4A is an illustration showing a closed version of the chamber having an access door, in accordance with another embodiment of the present invention.
Figure 4B:
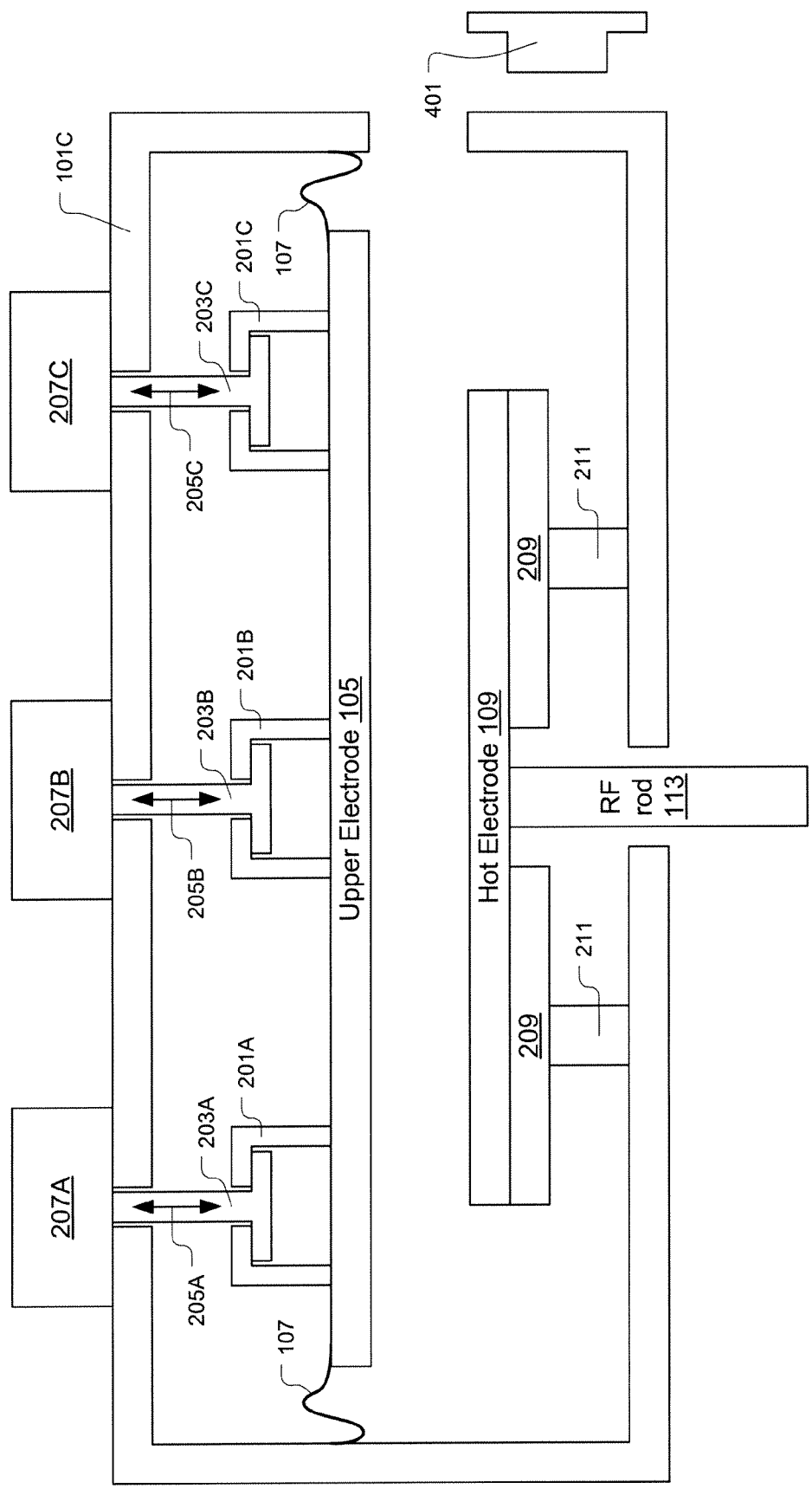
FIG. 4B is an illustration showing the closed version of the chamber with the access door removed, in accordance with another embodiment of the present invention.

FIG. 4A is an illustration showing a closed version of the chamber 101C having an access door 401, in accordance with another embodiment of the present invention. The access door 401 is defined to be removed from the chamber 101C to enable access to the interior of the chamber 101C for placement and retrieval of the of the part 111 and for changing the hot electrode 109. FIG. 4B is an illustration showing a closed version of the chamber 101C with the access door 401 removed, in accordance with another embodiment of the present invention. In various embodiments, the access door 401 can be secured to the chamber 101C in a number of ways, such as through fasteners or clamps. It should be appreciated, however, that regardless of the technique used to secure the access door 401 to the chamber 101C, the access door 401 should be secured so as to establish a substantially uniform ground potential between the interface of the access door 401 and the chamber 101C.

In one embodiment, the apparatus 100 is defined to operate at natural atmospheric and room temperature conditions. However, in another embodiment, the apparatus 100 is defined to provide a controlled environment within the chamber 101 interior cavity 102 during operation of the apparatus 100. The controlled environment can include a controlled atmosphere and temperature within the chamber 101 interior cavity 102. In one embodiment, the atmospheric conditions (such as gas content, moisture level, pressure, etc.) and temperature within the chamber 101 interior cavity 102 is controlled to substantially emulate atmospheric conditions and temperature to which the part 111 will be exposed during operation of the plasma processing system within which the part 111 will be deployed. It should be appreciated that in this embodiment, a number of gas input and output ports can be disposed within the chamber 101 so as to enable supply and removal of various gas mixtures to/from the chamber 101 interior cavity 102. Also, it should be appreciated that in this embodiment a number of support systems can be plumbed to the number of gas input and output ports. These support systems can include gas supply systems, pressurization systems, vacuum systems, gas heating and/or cooling systems, etc., as necessary to establish the appropriate controlled atmospheric conditions and temperature with the chamber 101 interior cavity 102.

Determining Capacitance and Dielectric Constant of Part

Figure 6:
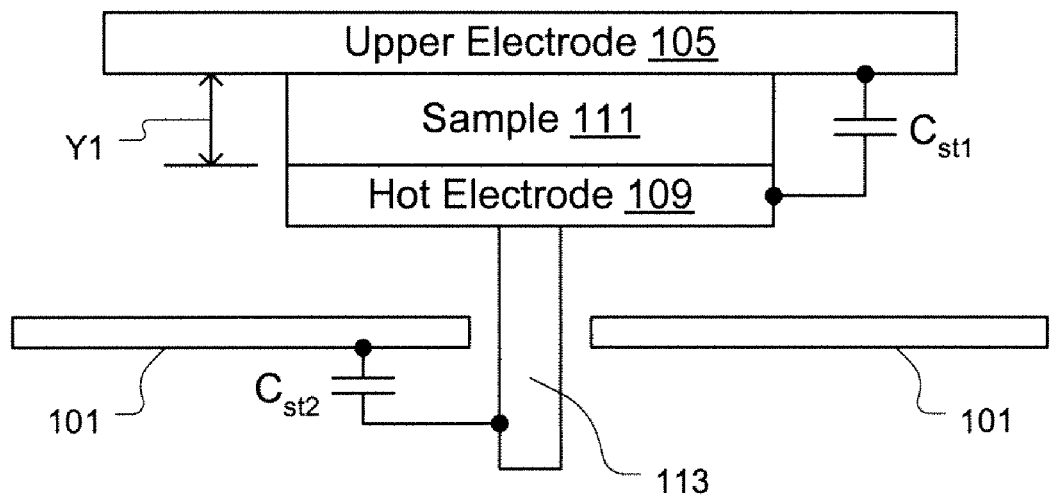
FIG. 6 is an illustration depicting capacitances between the hot electrode/RF rod and the grounded upper electrode/chamber when the exemplary part is disposed between the upper electrode and the hot electrode, in accordance with one embodiment of the present invention.

FIG. 6 is an illustration depicting capacitances between the hot electrode 109/RF rod 113 and the grounded upper electrode 105/chamber 101 when the exemplary part 111 is disposed between the upper electrode 105 and the hot electrode 109, in accordance with one embodiment of the present invention. As shown in FIG. 6, the capacitance between the upper electrode 105 and the hot electrode 109 is defined by the capacitance ($C_{part}$) of the part 111 and the capacitance ($C_{st1}$) between the hot electrode 109 and the portions of the upper electrode 105 outside of the contact region between the part 111 and the upper electrode 105. Also, a capacitance ($C_{st2}$) exists between the RF rod 113 and the chamber 101 bottom. It should be understood that the capacitances ($C_{st1}$) and ($C_{st2}$) are functions of the separation distance (Y1) between the upper electrode 105 and the hot electrode 109. Also, the capacitance ($C_{part}$) is a function of the dielectric constant of the part ($k_{part}$). Because the capacitances ($C_{part}$), ($C_{st1}$), and ($C_{st2}$) represent parallel capacitances, the total capacitance ($C_{total\_with\_part}$) between the hot electrode 109/RF rod 113 and the grounded upper electrode 105/chamber 101 is defined as a sum of the capacitances ($C_{part}$), ($C_{st1}$), and ($C_{st2}$), as shown in Equation 1.

$$(C_{total\_with\_part}) = (C_{part}\{k_{part}\}) + (C_{st1}\{Y1\}) + (C_{st2}\{Y1\})$$ Equation 1

Figure 7:
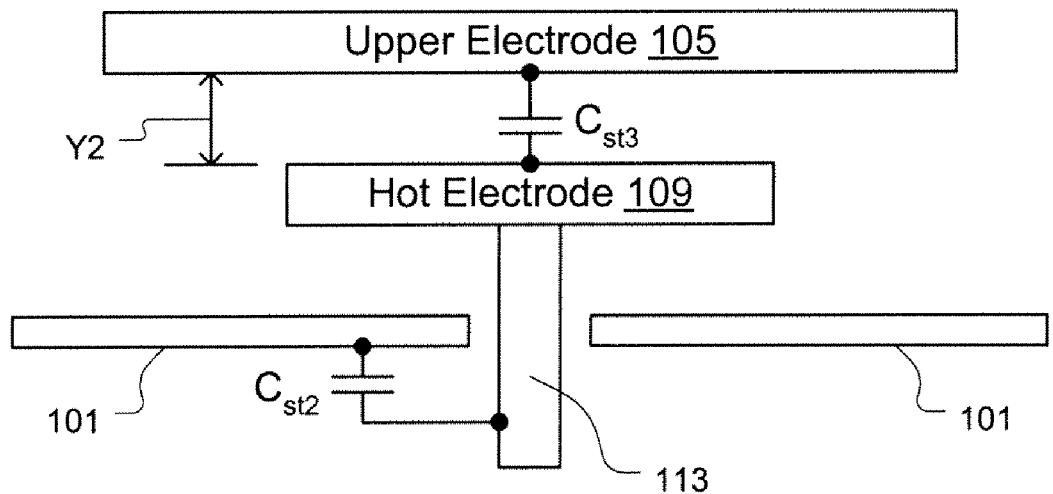
FIG. 7 is an illustration depicting capacitances between the hot electrode/RF rod and the grounded upper electrode/chamber when there is no part disposed between the upper electrode and the hot electrode, in accordance with one embodiment of the present invention.

FIG. 7 is an illustration depicting capacitances between the hot electrode 109/RF rod 113 and the grounded upper electrode 105/chamber 101 when there is no part disposed between the upper electrode 105 and the hot electrode 109, in accordance with one embodiment of the present invention. As shown in FIG. 7, the capacitance between the upper electrode 105 and the hot electrode 109 is defined by the capacitance ($C_{st3}$) of the atmosphere within the chamber 101 interior cavity. Also, as in FIG. 6, the capacitance ($C_{st2}$) exists between the RF rod 113 and the chamber 101 bottom. It should be understood that the capacitances ($C_{st3}$) and ($C_{st2}$) in FIG. 7 are functions of the separation distance (Y2) between the upper electrode 105 and the hot electrode 109. Because the capacitances ($C_{st3}$) and ($C_{st2}$) represent parallel capacitances, the total capacitance ($C_{total\_without\_part}$) between the hot electrode 109/RF rod 113 and the grounded upper electrode 105/chamber 101 is defined as a sum of the capacitances ($C_{st3}$) and ($C_{st2}$), as shown in Equation 2.

$$(C_{total\_without\_part}) = (C_{st3}\{Y2\}) + (C_{st2}\{Y2\})$$ Equation 2

In the configuration of FIG. 6, with the upper electrode 105 resting on top of the part 111 positioned in a substantially centered manner on top of the hot electrode 109, the variable capacitor 123 can be adjusted to achieve a particular resonance frequency of the apparatus 100. Because dielectric properties of the part 111 are frequency dependent, in one embodiment, the resonance frequency of the apparatus 100 is set to the operating frequency of the RF power that is to be used in the plasma process to which the part 111 will be exposed when deployed in the plasma processing system. Thus, the apparatus 100 according to the configuration of FIG. 6 with the part 111 present in the chamber 101 will have a particular resonance frequency.

With reference to the configuration of FIG. 7 with the part absent, it should be understood that the resonance frequency of the RF power will change as the distance (Y2) between the upper electrode 105 and the hot electrode 109 is changed. In the configuration of FIG. 7, the variable capacitor 123 and RF signal generator 125 are maintained at their respective settings as applied in the configuration of FIG. 6 with the part 111 present in the chamber 101. Under these conditions, the upper electrode 105 in the configuration of FIG. 7 (without the part present) can be lowered toward the hot electrode 109 until the resonance frequency of the apparatus 100 according to the configuration of FIG. 7 substantially matches the resonance frequency of the apparatus 100 according to the configuration of FIG. 6 (with the part 111 present). When the upper electrode 105 is lowered to cause the substantial matching between the resonance frequencies of the configurations of FIGS. 6 and 7, the total capacitance ($C_{total\_with\_part}$) of configuration 6 will be substantially equivalent to the total capacitance ($C_{total\_without\_part}$) of configuration 7. In this situation, Equations 1 and 2 can be set equal to each other as shown in Equation 3.

$$(C_{part}\{k_{part}\})+(C_{st1}\{Y1\})+(C_{st2}\{Y1\})= (C_{total\_without\_part}) \qquad \text{Equation 3}$$

The right side of Equation 3, ($C_{total\_without\_part}$) at the resonance frequency, can be measured directly by connecting a capacitance meter between the RF rod 113 and the upper electrode 105, with the RF rod 113 disconnected from the conductor plate 115 and the upper electrode 105 maintained at the vertical elevation corresponding to the resonance frequency when the part is absent. Also, the capacitance ($C_{st1}\{Y1\}$) between the hot electrode 109 and the portions of the upper electrode 105 outside of the contact region between the part 111 and the upper electrode 105 in the configuration of FIG. 6 can be simulated. Also, the capacitance ($C_{st2}\{Y1\}$) between the RE rod 113 and the chamber 101 bottom in the configuration of FIG. 6 can be simulated. In one embodiment, the capacitances ($C_{st1}\{Y1\}$) and ($C_{st2}\{Y1\}$) are simulated through a finite element model analysis of the configuration of FIG. 6. With the capacitances ($C_{total\_without\_part}$), ($C_{st1}\{Y1\}$), and ($C_{st2}\{Y1\}$) known, the capacitance of the part ($C_{part}\{k_{part}\}$) can be calculated, as shown in Equation 4.

$$(C_{part}\{k_{part}\})=(C_{total\_without\_part})-(C_{st1}\{Y1\})- (C_{st2}\{Y1\}) \qquad \text{Equation 4}$$

Figure 8:
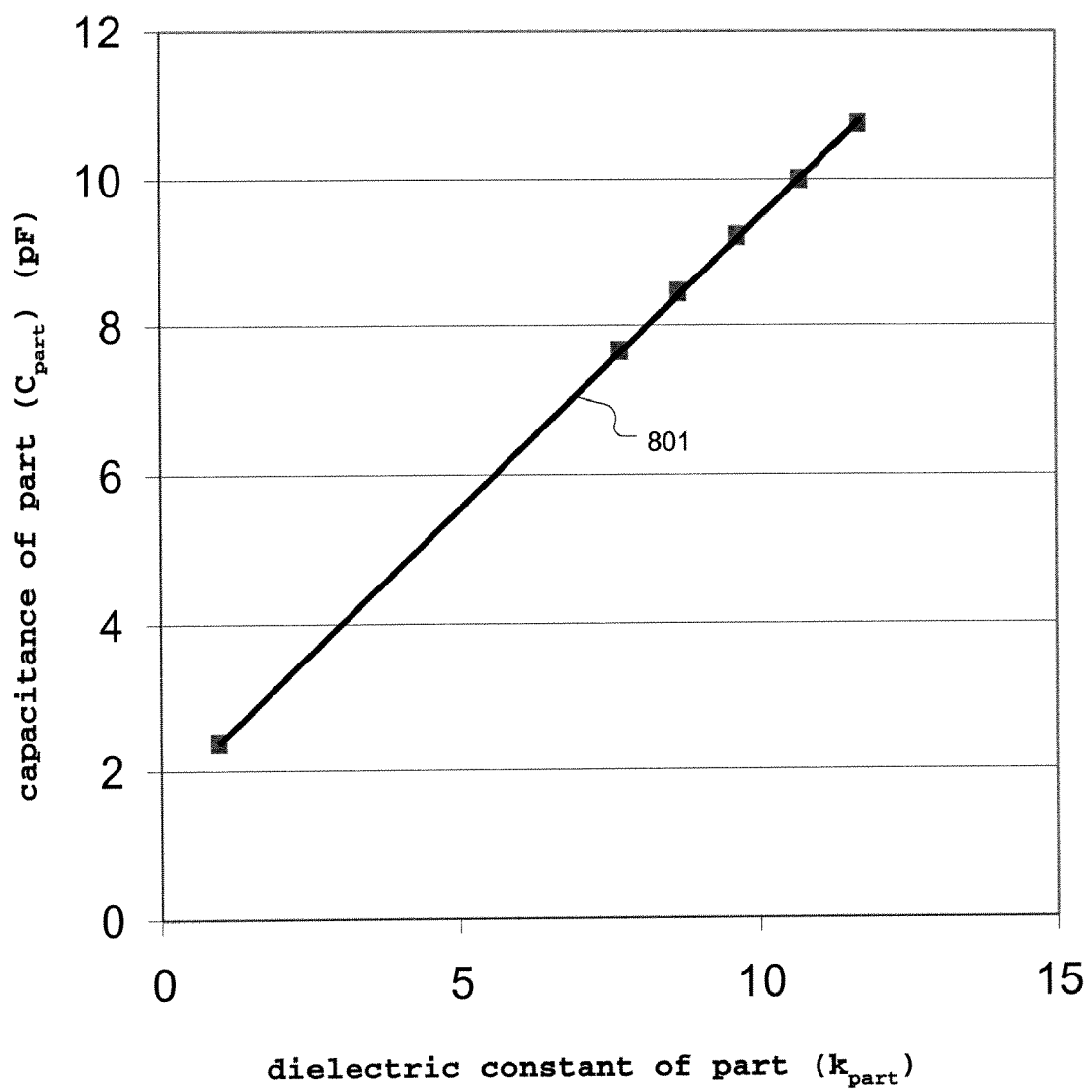
FIG. 8 is an illustration showing an exemplary curve of part capacitance ($C_{part}$) versus part dielectric constant ($k_{part}$)

Once the capacitance of the part ($C_{part}\{k_{part}\}$) is calculated, the dielectric constant of the part ($k_{part}$) can be determined based on the calculated capacitance of the part ($C_{part}\{k_{part}\}$). In one embodiment, the capacitance of the part ($C_{part}$), as disposed between the upper electrode 105 and the hot electrode 109, is simulated for a number of different assumed part dielectric constant ($k_{part}$) values, so as to enable generation of a curve of part capacitance ($C_{part}$) versus part dielectric constant ($k_{part}$). FIG. 8 is an illustration showing an exemplary curve 801 of part capacitance ($C_{part}$) versus part dielectric constant ($k_{part}$). Because the part capacitance ($C_{part}$) is a linear function of the part dielectric constant ($k_{part}$), the curve of part capacitance ($C_{part}$) versus part dielectric constant ($k_{part}$) will generally be a well-fit line, as illustrated by the curve 801 in FIG. 8. In one embodiment, the simulation of the part capacitance ($C_{part}$) for the number of different assumed part dielectric constant ($k_{part}$) values is performed through a finite element model analysis of the part 111 disposed between the upper electrode 105 and hot electrode 109. However, in another embodiment, if the geometric configurations of the part 111, the upper electrode 105, and the hot electrode 109 are sufficiently simple, the part capacitance ($C_{part}$) for the number of different assumed part dielectric constant ($k_{part}$) values may be determined analytically. Using the generated curve of part capacitance ($C_{part}$) versus part dielectric constant ($k_{part}$), and the actual capacitance of the part ($C_{part}$) as calculated using Equation 4, the actual dielectric constant of the part ($k_{part}$) can be determined.

Figure 9:
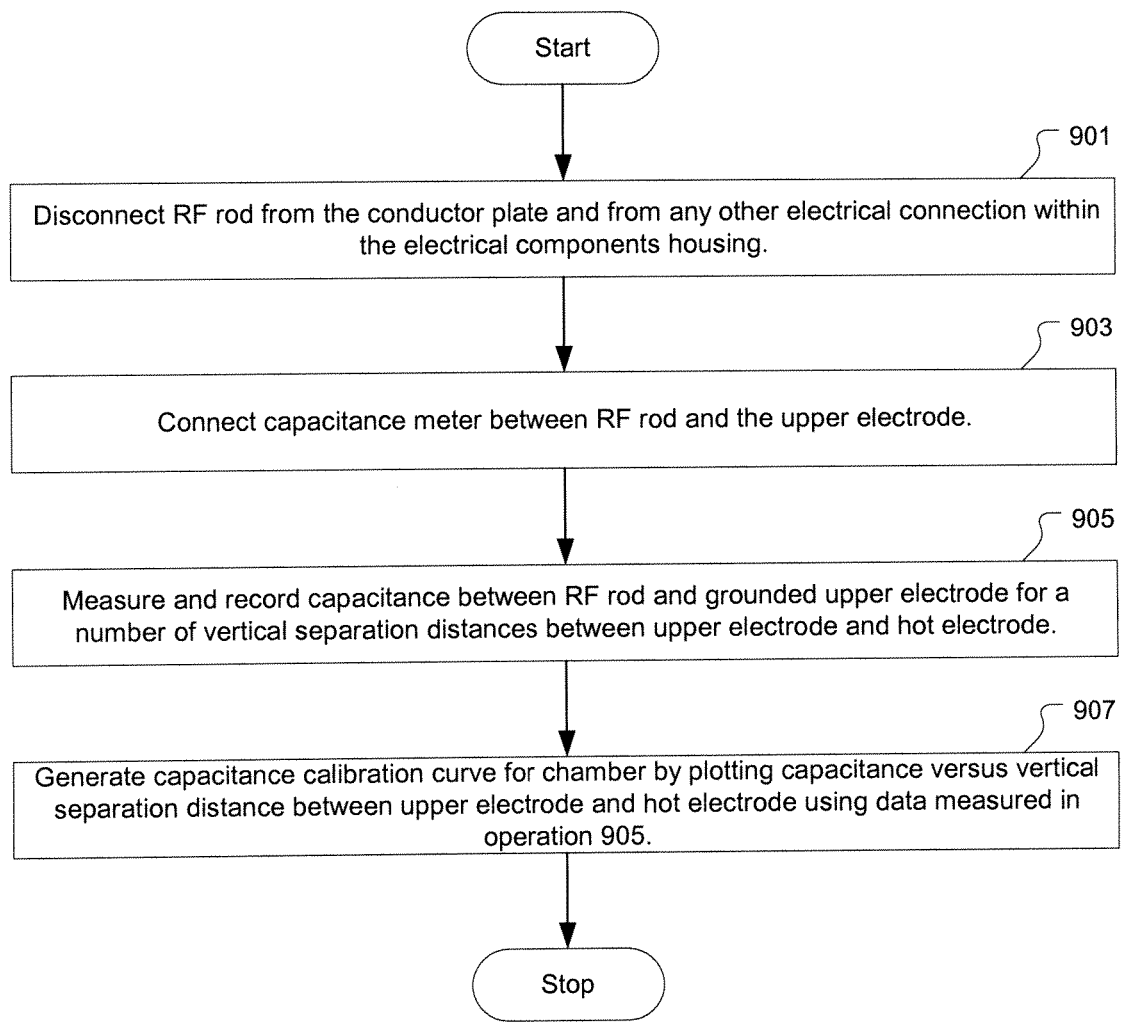
FIG. 9 is an illustration showing a flowchart of a method for calibrating the relationship between the total capacitance ($C_{total\_without\_part}$) and the separation distance between the upper electrode and the hot electrode, in accordance with one embodiment of the present invention.

As discussed above, to determine the total capacitance ($C_{total\_without\_part}$) at the resonance frequency, it is necessary to know the relationship between the total capacitance ($C_{total\_without\_part}$) and the separation distance between the upper electrode 105 and the hot electrode 109. FIG. 9 is an illustration showing a flowchart of a method for calibrating the relationship between the total capacitance ($C_{total\_without\_part}$) and the separation distance between the upper electrode 105 and the hot electrode 109, in accordance with one embodiment of the present invention. In an operation 901, the RF rod 113 is disconnected from the conductor plate 115 and from any other electrical connection within the electrical components housing 103. In an operation 903, a capacitance meter is connected between the RF rod 113 and the upper electrode 105. In an operation 905, using the capacitance meter, the capacitance between the RF rod 113 and grounded upper electrode 105 is measured and recorded for a number of vertical separation distances between the upper electrode 105 and the hot electrode 109. In one embodiment, operation 905 is performed by positioning the upper electrode 105 at a number of vertical separation distances from the hot electrode 109 extending from 0.05 inch to 1.2 inch, in increments of 0.05 inch. In the operation 905, at each vertical separation distance between the upper electrode 105 and the hot electrode 109, the upper electrode 105 is maintained in a substantially level horizontal orientation so as to be substantially parallel to the hot electrode 109. The method further includes an operation 907 for generating a capacitance calibration curve for the chamber 101 by plotting the capacitance versus vertical separation distance between the upper electrode 105 and the hot electrode 109 using the data measured in operation 905. The capacitance calibration curve for the chamber 101 can be repeatedly used to determine the total capacitance ($C_{total\_without\_part}$) at the resonance frequency once the vertical elevation of the upper electrode 105 at the resonance frequency (without the part present) is determined.

Figure 10:
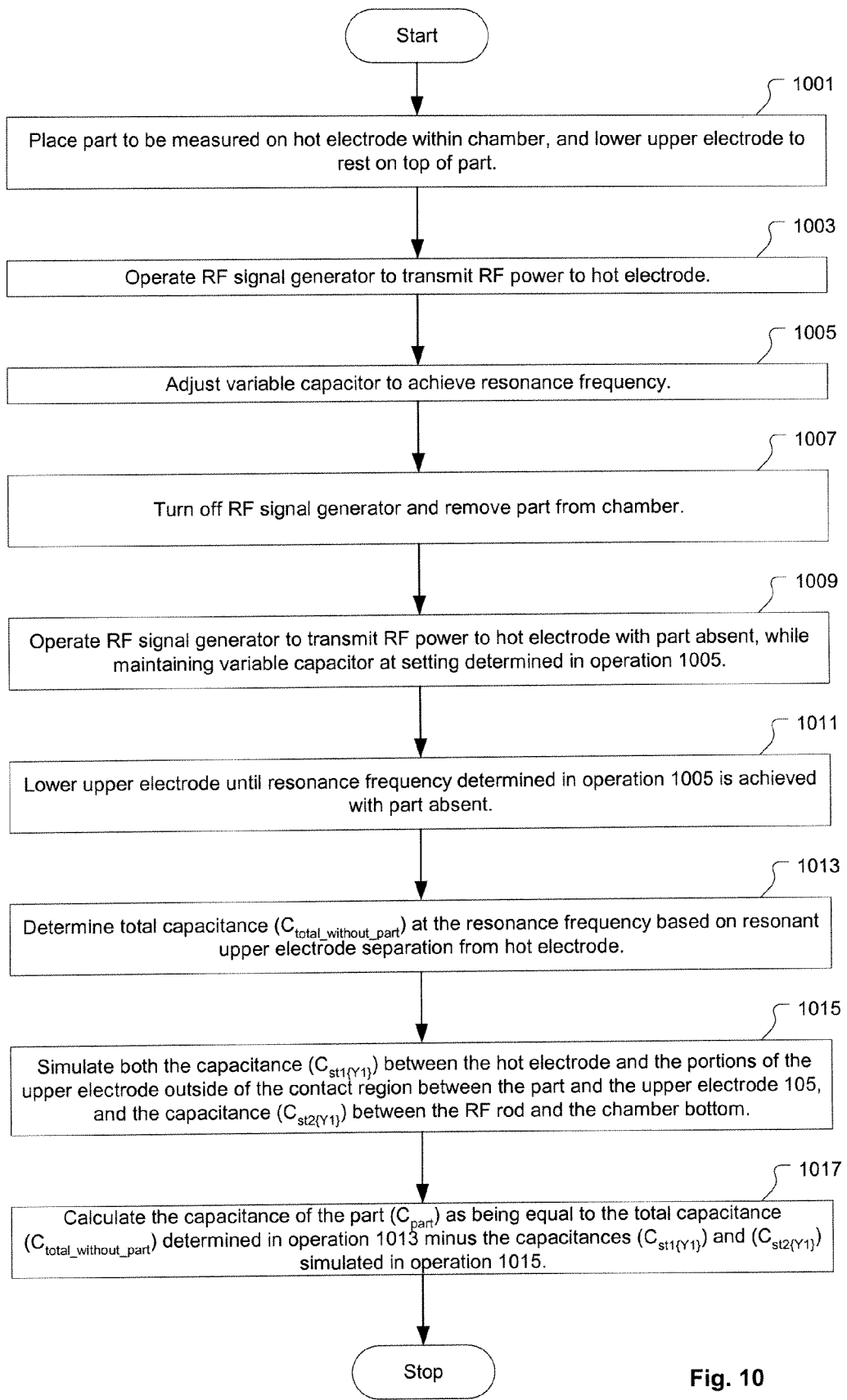
FIG. 10 is an illustration showing a method for determining a capacitance of a part ($C_{part}$), in accordance with one embodiment of the present invention.

FIG. 10 is an illustration showing a method for determining a capacitance of a part ($C_{part}$), in accordance with one embodiment of the present invention. The method of FIG. 10 is a representation the procedure as described above. The method includes an operation 1001 for placing a part to be measured on the hot electrode 109 within the chamber 101, and for lowering the upper electrode 105 to rest on top of the part. In one embodiment, alignment pins are used to enable precise positioning and alignment of the part on the hot electrode 109. In an operation 1003, the RF signal generator 125 is operated to transmit RF power to the hot electrode 109. In an operation 1005, the variable capacitor 123 is adjusted to achieve the resonance frequency, i.e., peak frequency, of the RF power. In one embodiment, the resonance frequency corresponds to a peak gain between the connector 129 and the connector 131 of the electrical components housing 103. In this embodiment, the RF voltmeter 127 can be monitored to identify when the variable capacitor 123 setting corresponds to the peak gain between the connectors 129 and 131, and thereby corresponds to the resonance frequency of the apparatus 100.

The method further includes an operation 1007 for turning off the RF signal generator 125 and removing the part from the chamber. In an operation 1009, the RF signal generator 125 is operated to transmit RF power to the hot electrode 109 with the part absent. In the operation 1009, the variable capacitor 123 is maintained at the setting determined in operation 1005. In an operation 1011, the upper electrode 105 is lowered until the resonance frequency determined in operation 1005 is achieved with the part absent. In one embodiment, the RF voltmeter 127 can be monitored to identify when the upper electrode 105 elevation causes the peak gain between the connectors 129 and 131 to be reached, and thereby causes the resonance frequency to be achieved. The vertical separation distance between the upper electrode 105 and the hot electrode 109 at the resonance frequency with the part absent is called the resonant upper electrode 105 separation.

Once the resonant upper electrode 105 separation is determined, an operation 1013 is performed to determine the total capacitance ($C_{total\_without\_part}$) at the resonance frequency based on the resonant upper electrode 105 separation. In one embodiment, the capacitance calibration curve for the chamber 101, as generated in the method of FIG. 9, is used to determine the total capacitance ($C_{total\_without\_part}$) at the resonance frequency in operation 1013.

The method further includes an operation 1015 for simulating both the capacitance ($C_{st1}\{Y1\}$) between the hot electrode 109 and the portions of the upper electrode 105 outside of the contact region between the part 111 and the upper electrode 105, and the capacitance ($C_{st2}\{Y1\}$) between the RE rod 113 and the chamber 101 bottom. As previously mentioned, in one embodiment, the capacitances ($C_{st1}\{Y1\}$) and ($C_{st2}\{Y1\}$) can be simulated through a finite element model analysis. An operation 1017 is then performed to calculate the capacitance of the part ($C_{part}$) as being equal to the total capacitance ($C_{total\_without\_part}$) determined in operation 1013 minus the capacitances ($C_{st1}\{Y1\}$) and ($C_{st2}\{Y1\}$) simulated in the operation 1015.

Figure 11:
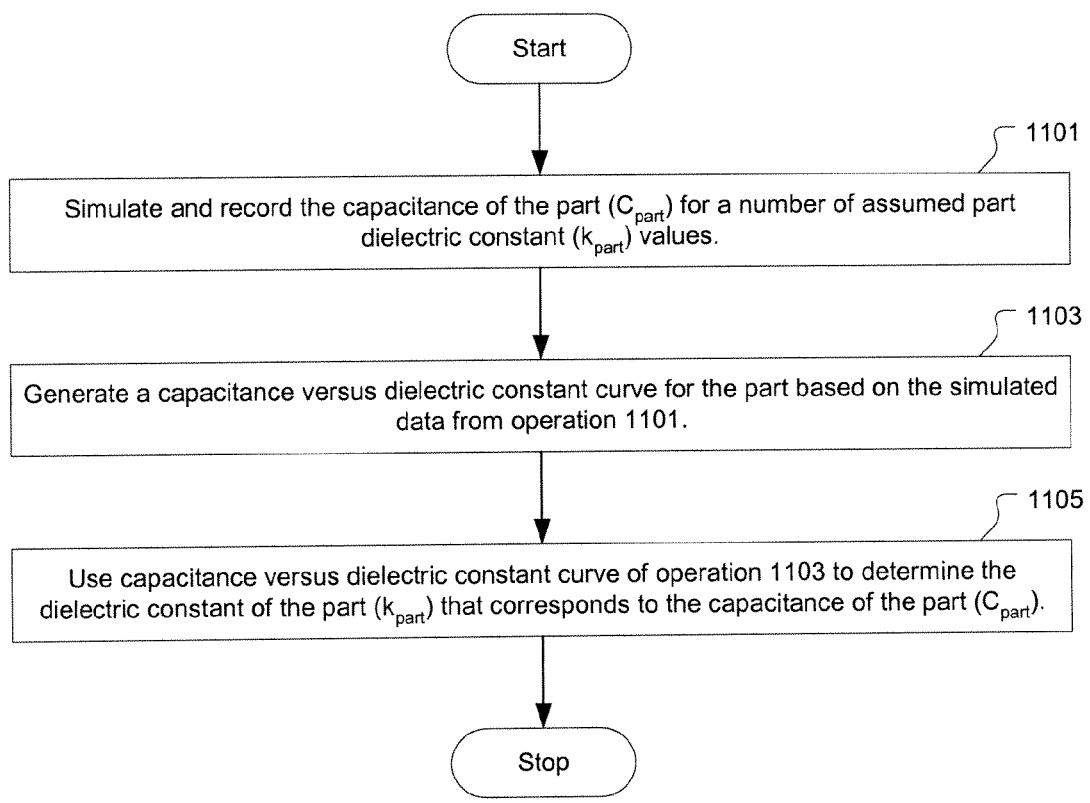
FIG. 11 is an illustration showing a flowchart of a method for determining the dielectric constant of the part ($k_{part}$), in accordance with one embodiment of the present invention.

FIG. 11 is an illustration showing a flowchart of a method for determining the dielectric constant of the part ($k_{part}$), in accordance with one embodiment of the present invention. In an operation 1101, the capacitance of the part ($C_{part}$) is simulated and recorded for a number of assumed part dielectric constant ($k_{part}$) values. In an operation 1103, a capacitance versus dielectric constant curve, such as the example shown in FIG. 8, is generated for the part based on the simulated data from operation 1101. In an operation 1105, the capacitance versus dielectric constant curve of operation 1103 is used to determine the dielectric constant of the part ($k_{part}$) that corresponds to the capacitance of the part ($C_{part}$) as determined in the method of FIG. 10.

Determining Loss Tangent of Part

Figure 12:
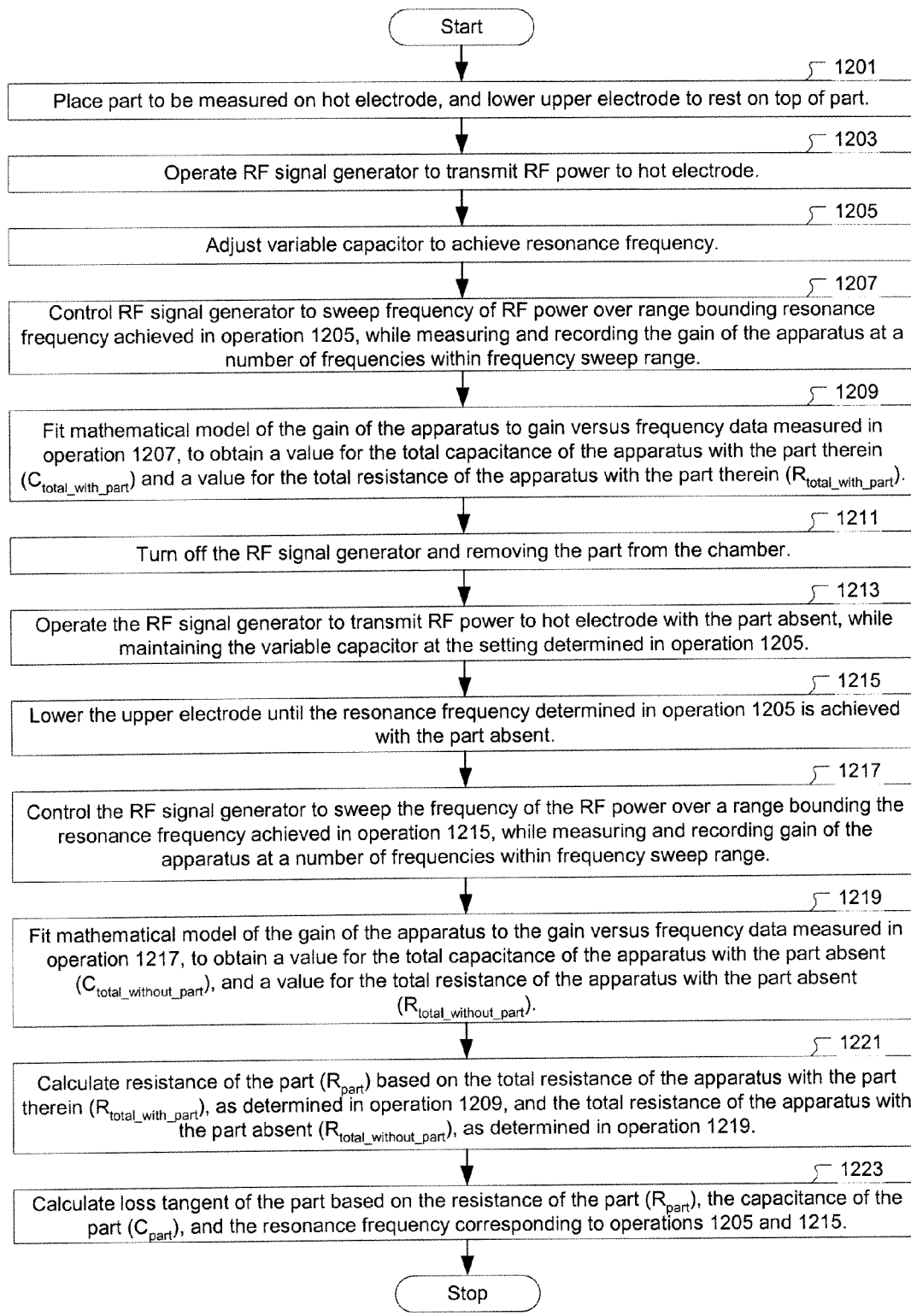
FIG. 12 is an illustration showing a flowchart of a method for determining a loss tangent of a part, in accordance with one embodiment of the present invention.

FIG. 12 is an illustration showing a flowchart of a method for determining a loss tangent of a part, in accordance with one embodiment of the present invention. The method includes an operation 1201 for placing a part to be measured on the hot electrode 109 within the chamber 101, and for lowering the upper electrode 105 to rest on top of the part. In an operation 1203, the RF signal generator 125 is operated to transmit RF power to the hot electrode 109. In an operation 1205, the variable capacitor 123 is adjusted to achieve the resonance frequency, i.e., peak frequency, of the RF power. In one embodiment, the resonance frequency corresponds to a peak gain between the connectors 129 and 131 of the electrical components housing 103. In this embodiment, the RF voltmeter 127 can be monitored to identify when the variable capacitor 123 setting corresponds to the peak gain between the connectors 129 and 131, and thereby corresponds to the resonance frequency of the apparatus 100.

The method continues with an operation 1207 in which the RF signal generator 125 is controlled to sweep the frequency of the RF power over a range bounding the resonance frequency achieved in operation 1205, while using the RF voltmeter 127 to measure and record the gain of the apparatus 100 between the connections 129 and 131 at a number of frequencies within the frequency sweep range. In one embodiment, the frequency range covered by the frequency sweep of operation 1207 is defined to include a 3 dB variation in gain of the apparatus 100 on each side of the peak gain corresponding to the resonance frequency. The method further includes an operation 1209 for fitting a mathematical model of the gain of the apparatus 100 to the gain versus frequency data measured in operation 1207, wherein the fitting of operation 1209 provides a value for the total capacitance of the apparatus 100 with the part therein ($C_{total\_with\_part}$) and a value for the total resistance of the apparatus 100 with the part therein ($R_{total\_with\_part}$). The fitting of operation 1209 is further described below with regard to FIGS. 13-14 and Equation 5.

Figure 13:
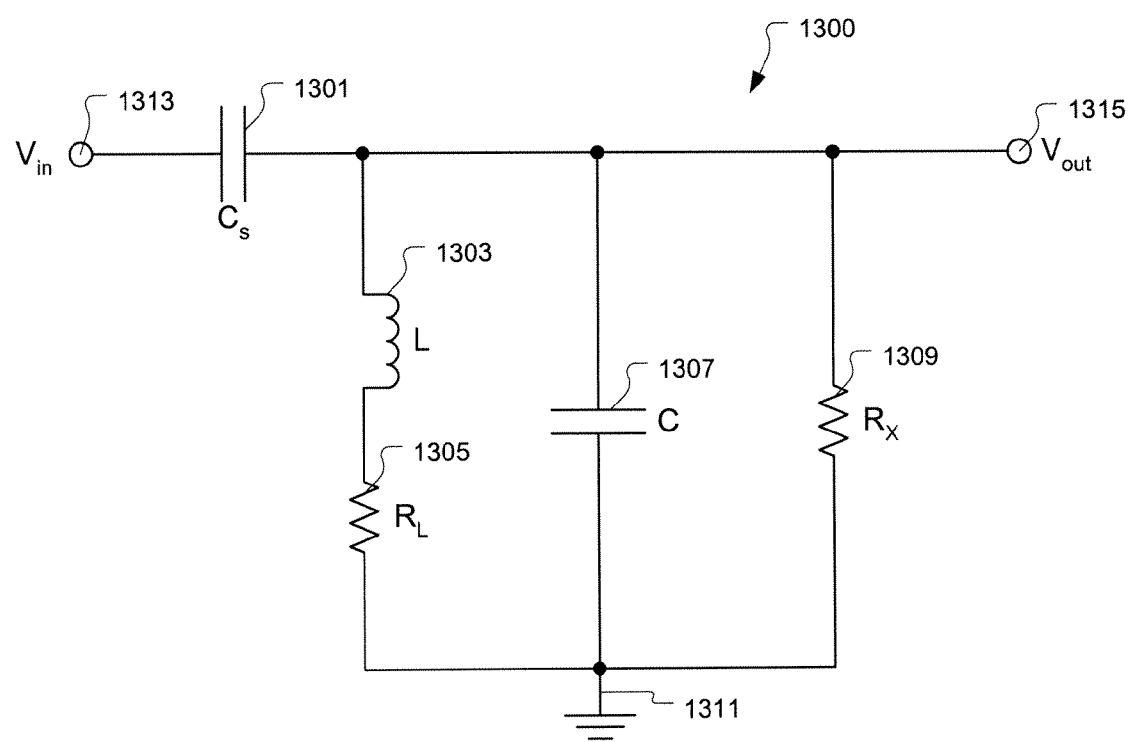
FIG. 13 is an illustration showing an equivalent electrical circuit representation of the apparatus with the part disposed between the upper electrode and hot electrode, as depicted in FIG. 1, in accordance with one embodiment of the present invention.

FIG. 13 is an illustration showing an equivalent electrical circuit representation 1300 of the apparatus 100 with the part 111 disposed between the upper electrode 105 and hot electrode 109, as depicted in FIG. 1, in accordance with one embodiment of the present invention. A node 1313 corresponds to the connector 129 of the electrical components housing 103. A node 1315 corresponds to the connector 131 of the electrical components housing 103. The RF voltmeter 127 connected to connectors 129 and 131 is capable of measuring a gain of the apparatus 100 as defined by $|V_{out}/V_{in}|$. With regard to FIG. 1, the equivalent electrical circuit 1300 includes a capacitance ($C_s$) 1301 representing the capacitor 117, an inductance (L) 1303 and resistance ($R_L$) 1305 representing the inductor 119, a capacitance (C) 1307 representing the total capacitance of the apparatus 100, a resistance ($R_X$) 1309 representing the total resistance of the apparatus 100, and a ground potential 1311. It should be understood that the capacitance (C) 1307 represents the combination of the capacitors 121 and 123, the capacitance between the RF rod 113/hot electrode 109 and chamber 101/upper electrode 105, and the capacitance of the part 111 if present.

Equation 5 defines the gain of the apparatus 100 as a function of the electrical components within the equivalent electrical circuit 1300 of FIG. 13. In Equation 5, (f) is the frequency of the RF power corresponding to the gain, (C) is the total capacitance of the apparatus 100, and ($R_X$) is the total resistance of the apparatus 100. In Equation 5, the parameters ($C_s$), (L), ($R_L$) are known from the electrical components in the electrical components housing 103. Therefore, in Equation 5, the parameters (C) and ($R_X$) represent the unknown parameters.

$$\text{Gain} = \left| \frac{1}{\left( -\frac{i}{2C_s f \pi} + \frac{1}{2iCf\pi + \frac{1}{2fi\pi L + R_L} + \frac{1}{R_X}} \right) \left( 2iCf\pi + \frac{1}{2fi\pi L + R_L} + \frac{1}{R_X} \right)} \right| \quad \text{Equation 5}$$

Figure 14:
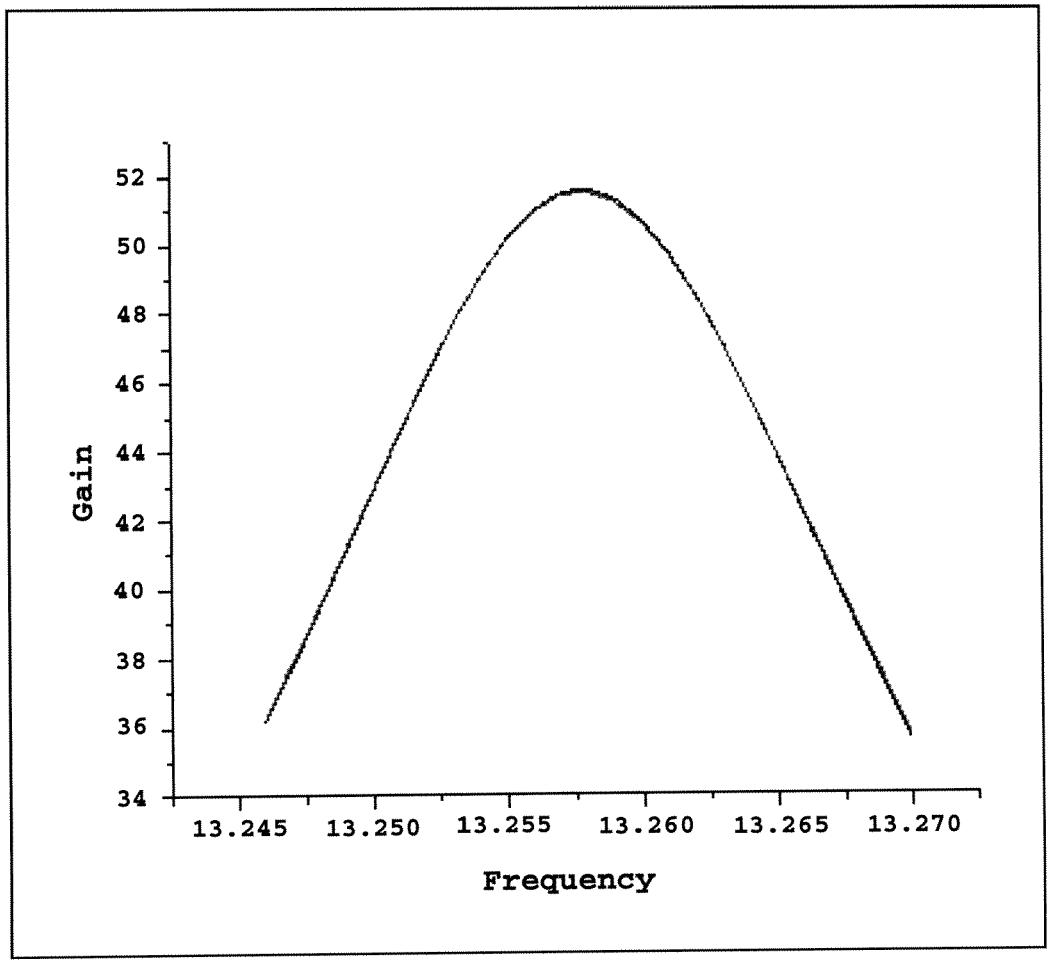
FIG. 14 is an illustration showing an exemplary fitting of Equation 5 based on gain versus frequency data measured and recorded in a frequency sweep of operation.

In the operation 1209, Equation 5 is fit to the gain versus frequency data measured in operation 1207 with the part present in the apparatus 100, thereby yielding a value for the total capacitance of the apparatus 100 with the part therein, i.e., (C)=($C_{total\_with\_part}$) and a value for the total resistance of the apparatus 100 with the part therein, i.e., ($R_X$)=($R_{total\_with\_part}$). FIG. 14 is an illustration showing an exemplary fitting of Equation 5 in accordance with operation 1209, based on gain versus frequency data measured and recorded in the frequency sweep of operation 1207. In one embodiment, a multivariate regression technique is used to fit Equation 5 to the measured gain versus frequency data in operation 1209. Also, in one embodiment, a confidence interval for each of the unknown parameters (C) and ($R_X$) is estimated by Monte Carlo simulation.

The method of FIG. 12 continues with an operation 1211 for turning off the RF signal generator 125 and removing the part from the chamber. In an operation 1213, the RF signal generator 125 is operated to transmit RF power to the hot electrode 109 with the part absent. In the operation 1213, the variable capacitor 123 is maintained at the setting determined in operation 1205. In an operation 1215, the upper electrode 105 is lowered until the resonance frequency determined in operation 1205 is achieved with the part absent. In one embodiment, the RF voltmeter 127 can be monitored to identify when the upper electrode 105 elevation causes the peak gain between the connectors 129 and 131 to be reached, and thereby causes the resonance frequency to be achieved. As previously mentioned, the vertical separation distance between the upper electrode 105 and the hot electrode 109 at the resonance frequency with the part absent is called the resonant upper electrode 105 separation.

The method continues with an operation 1217 in which the RF signal generator 125 is controlled to sweep the frequency of the RE power over a range bounding the resonance frequency achieved in operation 1215, while using the RF voltmeter 127 to measure and record the gain of the apparatus 100 between the connections 129 and 131 at a number of frequencies within the frequency sweep range. In one embodiment, the frequency range covered by the frequency sweep of operation 1217 is defined to include a 3 dB variation in gain of the apparatus 100 on each side of the peak gain corresponding to the resonance frequency. The method further includes an operation 1219 for fitting a mathematical model of the gain of the apparatus 100, i.e., Equation 5, to the gain versus frequency data measured in operation 1217. The fitting of operation 1219 provides a value for the total capacitance of the apparatus 100 with the part absent, i.e., (C)=($C_{total\_without\_part}$), and a value for the total resistance of the apparatus 100 with the part absent ($R_X$)=($R_{total\_without\_part}$). As previously mentioned, a multivariate regression technique can be used to fit Equation 5 to the measured gain versus frequency data in operation 1219. Also, in one embodiment, a confidence interval for each of the unknown parameters (C) and ($R_X$) is estimated by Monte Carlo simulation.

The method continues with an operation 1221 for calculating the resistance of the part ($R_{part}$) based on the total resistance of the apparatus 100 with the part therein ($R_{total\_with\_part}$), as determined in operation 1209, and the total resistance of the apparatus 100 with the part absent ($R_{total\_without\_part}$), as determined in operation 1219. More specifically, the resistance of the part ($R_{part}$) is determined using Equation 6.

$$\frac{1}{R_{part}} = \frac{1}{R_{total\_without\_part}} - \frac{1}{R_{total\_with\_part}} \Rightarrow \quad \text{Equation 6}$$

$$R_{part} = \frac{(R_{total\_with\_part})(R_{total\_without\_part})}{R_{total\_with\_part} - R_{total\_without\_part}}$$

The method then includes an operation 1223 for calculating the loss tangent of the part based on the resistance of the part ($R_{part}$), as determined in operation 1221, the capacitance of the part ($C_{part}$), as determined in the method of FIG. 10, and the resonance frequency, i.e., peak frequency, corresponding to operations 1205 and 1215. More specifically, the loss tangent of the part is determined using Equation 7.

$$\text{Loss Tangent of Part} = \frac{1}{(\text{Resonance Frequency})(R_{part})(C_{part})} \quad \text{Equation 7}$$

Based on the foregoing, it should be appreciated that the apparatus 100 and the associated methods (FIGS. 5B, 9, 10, 11, and 12) provide for measurement of the dielectric properties of actual full-size parts to be deployed in a plasma processing system. Also, the apparatus 100 and associated methods provide for measurement of the dielectric properties of parts at the actual operating frequency of the RF power to which the part will be exposed during plasma processing operations. Furthermore, the apparatus 100 and associated methods provide for measurement of the dielectric properties of parts under simulated atmospheric conditions and temperatures to which the part will be exposed during plasma processing operations. Additionally, the apparatus 100 and associated methods have been demonstrated to provide a loss tangent measurement repeatability having standard deviation of less than 1.24 E-5.

In one embodiment, the dielectric properties of the full-size part determined through use of the apparatus 100, such as the dielectric constant value and the loss tangent value, can be attached to the full-size part. In one embodiment, the determined dielectric constant and loss tangent values are embossed on the full-size part. For example, FIG. 5A shows an example of dielectric constant and loss tangent values embossed on the part 111A. In another embodiment, a tag is affixed to the full-size part to display the determined dielectric constant and loss tangent values. Additionally, the determined dielectric constant and loss tangent values of the full-size part can be stored on a computer readable medium, which can be supplied in conjunction with the full-size part.

With the above embodiments in mind, it should be understood that the invention can employ various computer-implemented operations involving data stored in computer systems. These operations are those requiring physical manipulation of physical quantities. Usually, though not necessarily, these quantities take the form of electrical or magnetic signals capable of being stored, transferred, combined, compared and otherwise manipulated. Further, the manipulations performed are often referred to in terms such as producing, identifying, determining, or comparing. Any of the operations described herein may be directed, controlled, or performed by a computer system. The computer system can be specially constructed for the required purpose, or the computer system can be a general-purpose computer selectively activated or configured by a computer program stored in the computer.

A computer program can be defined to control and monitor the apparatus 100 and perform the calculations associated with measuring the dielectric properties of a part utilizing the apparatus 100. Such a computer program can be defined to provide a graphical user interface (GUI) for enabling a user to control the apparatus 100, monitor a state of the apparatus 100, view data acquired by the apparatus 100, control calculations based on the data acquired by the apparatus 100, and view and record data/results generated through operation of the apparatus 100. Such a computer program can be embodied as computer readable code on a computer readable medium. The computer readable medium is any data storage device that can store data, which can be thereafter be read by a computer system. Examples of the computer readable medium include hard drives, network attached storage (NAS), read-only memory, random-access memory, CD-ROMs, CD-Rs, CD-RWs, magnetic tapes and other optical and non-optical data storage devices.

While this invention has been described in terms of several embodiments, it will be appreciated that those skilled in the art upon reading the preceding specifications and studying the drawings will realize various alterations, additions, permutations and equivalents thereof. Therefore, it is intended that the present invention includes all such alterations, additions, permutations, and equivalents as fall within the true spirit and scope of the invention.

The invention claimed is:

1. A method for characterizing dielectric properties of a part, comprising:
    placing a full-size part having its normal geometric configuration within a dielectric property measurement apparatus, wherein the dielectric property measurement apparatus includes an electrically grounded chamber, a lower electrode disposed within the chamber and connected to a radiofrequency (RF) transmission rod, and an electrically grounded upper electrode disposed within the chamber above the lower electrode, wherein the full-size part is placed on the lower electrode;
    positioning the electrically grounded upper electrode to rest freely on top of the full-size part such that a contact force between the electrically grounded upper electrode and the full-size part is defined only by a weight of the electrically grounded upper electrode;
    operating the dielectric property measurement apparatus to determine a dielectric constant value of the full-size part and a loss tangent value of the full-sized part; and
    attaching the determined dielectric constant and loss tangent values to the full-size part.

2. A method for characterizing dielectric properties of a part as recited in claim 1, wherein the dielectric property measurement apparatus is operated at a radiofrequency (RF) power having a frequency substantially equal to a frequency to which the full-size part is to be exposed during use of the full-size part.

3. A method for characterizing dielectric properties of a part as recited in claim 1, further comprising:
    exposing the full-size part to operational atmospheric conditions and operational temperatures during operation of the dielectric property measurement apparatus to determine the dielectric constant and the loss tangent values of the full-size part, wherein the operational atmospheric conditions and temperatures represent atmospheric conditions and temperatures to which the full-size part is to be exposed during use of the full-size part.

4. A method for characterizing dielectric properties of a part as recited in claim 1, wherein attaching the determined dielectric constant and loss tangent values to the full-size part is performed by embossing the determined dielectric constant and loss tangent values on the full-size part.

5. A method for characterizing dielectric properties of a part as recited in claim 1, wherein attaching the determined dielectric constant and loss tangent values to the full-size part is performed by affixing to the full-size part a tag displaying the determined dielectric constant and loss tangent values on the full-size part.

6. A method for characterizing dielectric properties of a part as recited in claim 1, wherein the full-size part is a dielectric component within a plasma processing system.

7. A method for characterizing dielectric properties of a part as recited in claim 1, further comprising:
    storing the determined dielectric constant and loss tangent values of the full-size part on a computer readable medium; and
    supplying the computer readable medium in conjunction with the full-size part.

8. A method for characterizing dielectric properties of a dielectric part of a plasma processing system, comprising:
    placing a full-size version of the dielectric part having its normal geometric configuration within a dielectric property measurement apparatus, wherein the dielectric property measurement apparatus includes an electrically grounded chamber, a lower electrode disposed within the chamber and connected to a radiofrequency (RF) transmission rod, and an electrically grounded upper electrode disposed within the chamber above the lower electrode, wherein the full-size version of the dielectric part is placed on the lower electrode;
    positioning the electrically grounded upper electrode to rest freely on top of the full-size version of the dielectric part such that a contact force between the electrically grounded upper electrode and the full-size version of the dielectric part is defined only by a weight of the electrically grounded upper electrode;
    operating the dielectric property measurement apparatus to determine a capacitance value of the dielectric part, a resistance value of the dielectric part, a dielectric constant value of the dielectric part, and a loss tangent value of the dielectric part; and
    embossing on the dielectric part each of the dielectric constant and loss tangent values of the dielectric part.

9. A method for characterizing dielectric properties of a dielectric part of a plasma processing system as recited in claim 8, wherein the dielectric property measurement apparatus is operated at a radiofrequency (RF) power having a frequency substantially equal to a frequency to which the dielectric part is to be exposed during its use within the plasma processing system.

10. A method for characterizing dielectric properties of a dielectric part of a plasma processing system as recited in claim 8, further comprising:
    exposing the dielectric part to operational atmospheric conditions and operational temperatures during operation of the dielectric property measurement apparatus to determine the capacitance, resistance, dielectric constant, and loss tangent values of the dielectric part, wherein the operational atmospheric conditions and temperatures represent atmospheric conditions and temperatures to which the dielectric part is to be exposed during its use within the plasma processing system.

* * * * *